US008555709B2

(12) United States Patent
Davison et al.

(10) Patent No.: US 8,555,709 B2
(45) Date of Patent: Oct. 15, 2013

(54) APPARATUSES AND METHODS FOR WIRELESS MONITORING AND CONTROL OF ENVIRONMENTAL SAMPLING AND CHROMATOGRAPHIC APPARATUSES

(75) Inventors: Dale A. Davison, Greenwood, NE (US); Dale L. Meyer, Lincoln, NE (US); Daniel G. Jameson, Roca, NE (US); Jack E. Silver, Lincoln, NE (US); Jon L. Curran, Lincoln, NE (US); Ruth A. Pipes, Odell, NE (US)

(73) Assignee: Teledyne Instruments, Inc., Thousand Oaks, CA (US)

( * ) Notice: Subject to any disclaimer, the term of this patent is extended or adjusted under 35 U.S.C. 154(b) by 1305 days.

(21) Appl. No.: 11/980,024

(22) Filed: Oct. 30, 2007

(65) Prior Publication Data
US 2008/0179251 A1 Jul. 31, 2008

Related U.S. Application Data

(62) Division of application No. 11/699,169, filed on Jan. 29, 2007, now abandoned.

(51) Int. Cl.
*G01N 1/28* (2006.01)
(52) U.S. Cl.
USPC ........ 73/61.55; 73/61.59; 422/48; 340/568.1; 436/180
(58) Field of Classification Search
USPC .............. 73/61.55, 61.59; 422/43, 48, 63, 67, 422/421; 340/568.1, 571; 436/180
See application file for complete search history.

(56) References Cited

U.S. PATENT DOCUMENTS

| 3,418,084 | A | * | 12/1968 | Allington | 422/70 |
| 4,168,955 | A | * | 9/1979 | Allington | 436/47 |
| 5,360,320 | A | * | 11/1994 | Jameson et al. | 417/4 |
| 5,544,683 | A | * | 8/1996 | Guhl | 141/65 |
| 5,690,893 | A | | 11/1997 | Ozawa et al. | |
| 6,427,526 | B1 | * | 8/2002 | Davison et al. | 73/61.55 |
| 6,458,273 | B1 | * | 10/2002 | Krakover et al. | 210/198.2 |
| 6,601,764 | B1 | | 8/2003 | Goodwin | |
| 6,971,506 | B2 | * | 12/2005 | Hassinen et al. | 198/803.14 |
| 6,981,640 | B2 | | 1/2006 | Routburg et al. | |
| 7,293,705 | B2 | | 11/2007 | Linton et al. | |
| 2001/0013494 | A1 | | 8/2001 | Maiefski et al. | |
| 2004/0178264 | A1 | | 9/2004 | Linton et al. | |
| 2004/0222297 | A1 | | 11/2004 | Dearing et al. | |
| 2004/0222298 | A1 | | 11/2004 | Dearing et al. | |
| 2004/0232230 | A1 | | 11/2004 | Linton et al. | |

(Continued)

OTHER PUBLICATIONS

Example of RFID Tag used on Chromatography Column, for at least 4 years by Waters Corporation on ACQUITY UPLC Console (eCord) and Document Details.

(Continued)

*Primary Examiner* — Terry Cecil
(74) *Attorney, Agent, or Firm* — Suiter Swantz pc llo

(57) ABSTRACT

A liquid chromatographic system includes columns, column mounting fixtures to which the columns are mounted, a detector, a collector, a controller and a plurality of RFIDs. A first RFID communicates with the controller and cooperating RFIDs mounted to other components provide information such as the history of components, parameters and the like. They also receive information from sensors relating to the operation of the liquid chromatograph, store the information and transmit it. Moreover, the RFIDs may substitute for hard wiring in many applications and may enable a central computer to control several liquid chromatographic system.

3 Claims, 9 Drawing Sheets

(56) References Cited

U.S. PATENT DOCUMENTS

| | | |
|---|---|---|
| 2004/0232231 A1 | 11/2004 | Linton et al. |
| 2005/0040952 A1 | 2/2005 | Dearing et al. |
| 2005/0125312 A1 | 6/2005 | Dearing et al. |
| 2005/0127177 A1 | 6/2005 | Dearing et al. |
| 2005/0178185 A1* | 8/2005 | Negri .................. 73/23.34 |
| 2005/0194437 A1 | 9/2005 | Dearing et al. |
| 2006/0015752 A1 | 1/2006 | Krueger |
| 2006/0027490 A1 | 2/2006 | DeMarco |
| 2006/0081705 A1 | 4/2006 | Linton et al. |
| 2006/0190628 A1 | 8/2006 | Linton et al. |
| 2006/0195563 A1 | 8/2006 | Chapin et al. |
| 2006/0283945 A1* | 12/2006 | Excoffier et al. ............. 235/439 |
| 2007/0069018 A1 | 3/2007 | Dearing et al. |
| 2007/0257111 A1 | 11/2007 | Ortenzi |

OTHER PUBLICATIONS

Waters Corporation Press Release Jan. 11, 2007, referring to ACQUITY UPLC system introduced 2004.

Waters Corporation Press Release Feb. 28, 2005 regarding new column chemistries for ACQUITY UPLC.

Pages from Waters Corporation website for nanoACQUITY UPLC System Overview, Enabling Technology and Related Solutions: UPLC and MS, before Jan. 17, 2007.

* cited by examiner

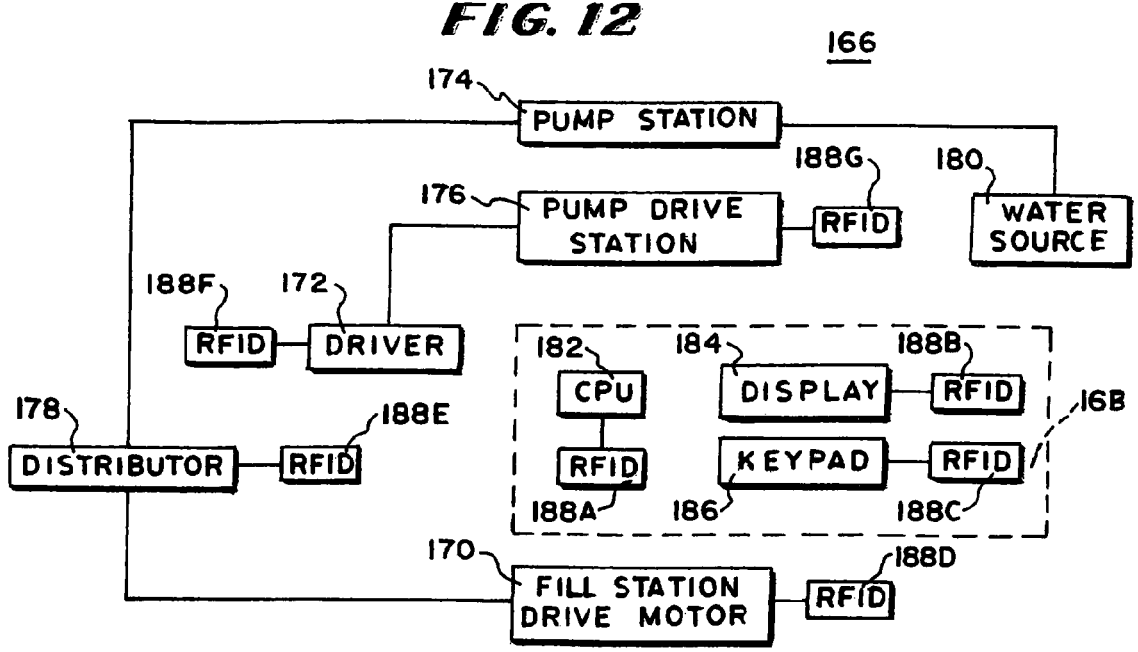
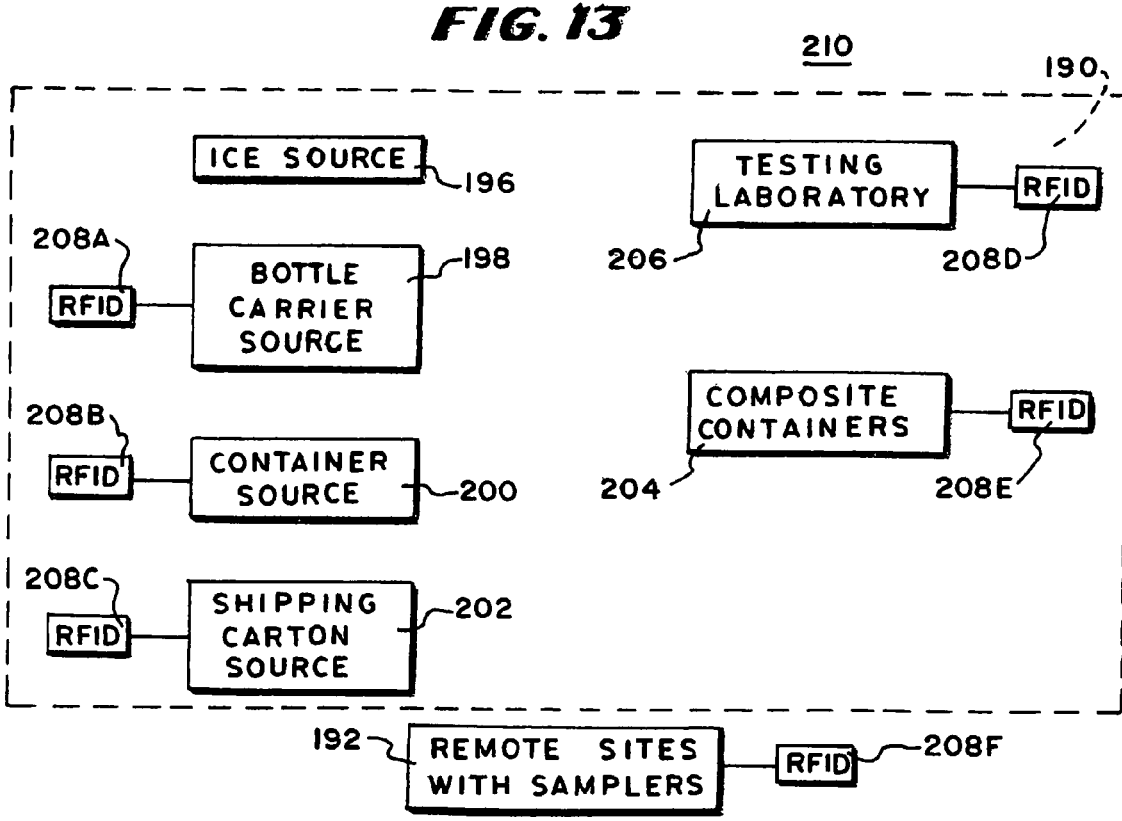

APPARATUSES AND METHODS FOR WIRELESS MONITORING AND CONTROL OF ENVIRONMENTAL SAMPLING AND CHROMATOGRAPHIC APPARATUSES

RELATED CASES

This application is a divisional application of parent U.S. application Ser. No. 11/699,169 filed Jan. 29, 2007, entitled APPARATUSES AND METHODS FOR WIRELESS MONITORING AND CONTROL OF ENVIRONMENTAL SAMPLING AND CHROMATOGRAPHIC APPARATUSES.

BACKGROUND OF THE INVENTION

This invention relates to apparatuses and methods for the wireless monitoring, identification and control of environmental and chromatographic apparatuses and synthetic chemistry.

Wireless communication for the purpose of monitoring, identifying and controlling devices and apparatus are known. For example RFID devices and Bluetooth devices are in widespread use to identify devices and transfer information to a receiver.

One prior art apparatus and method for identifying and providing information about a chromatographic column to a receiver is disclosed in U.S. Pat. No. 5,690,893 to Ozawa, et al., U.S. Pat. No. 6,971,506 to Hassinen and U.S. Pat. No. 6,458,273 to Krakover. U.S. Pat. No. 5,690,893 discloses a semi-conductor having a non-volitile memory embedded within it and storing information such as changes in the specification of the column, mixing ratios of eluent flow rate, theoretical plates and other information. The semi-conductor device is used for wireless communication to permit a data processor to receive the information stored in the semi-conductor U.S. Pat. No. 6,971,506 and U.S. Pat. No. 6,458,273 disclose a test tube carrier with an RFID tag on test tubes and a micro titer plate that is bar coded.

However, prior art wireless identification and communication techniques have not satisfactorily resolved many of the identification and communication problems that occur in liquid chromatography and environmental sampling.

SUMMARY OF THE INVENTION

Accordingly, it is an object of the invention to provide a novel wireless multiple fraction instrument and process such as for example, an instrument for wireless monitoring and control of environmental sampling apparatuses or chromatographic apparatuses.

It is a further object of the invention to provide a system for permitting chromatographic apparatuses to communicate with other chromatographic apparatuses.

It is a still further object of the invention to provide a system by which environmental apparatuses may communicate with other environmental apparatuses.

It is a still further object of the invention to provide a novel system for recording the past history of a chromatographic column on the column.

It is a still further object of the invention to provide a novel system for the wireless communication of environmental sampling apparatuses with other apparatuses.

It is a still further object of the invention to provide a novel system that enables a central microprocessor to control components on several chromatographic systems to coordinate or run them.

It is a still further object of the invention to provide a novel system which enables a microprocessor to control components of several environmental sample collectors.

It is a still further object of the invention to provide a novel system for providing to a controller a map or plan indicating the position of one or more sample containers.

It is a still further object of the invention to provide a novel system for indicating the position of an environmental sample container holder or a chromatographic tube rack or micro titer plate or the like.

It is a still further object of the invention to provide a novel system for indicating information on chromatographic columns intended to cooperate with both liquid chromatographic systems and other sample separating systems such as a mass spectrometer or gas chromatograph.

It is a still further object of the invention to provide a novel system for controlling robotic transport arrangements for moving a column from one separation system such as a liquid chromatographic system to another such as a mass spectrometer.

It is a still further object of the invention for providing a novel system for recording information on columns such as a calibration curve, retention times, packing, history, lot numbers, chromatograms, past separation conditions and the like.

It is a still further object of the invention to provide a novel system of inventory control in which a wireless communication system on chromatographic parts such as columns cooperate with a database recorded in a microprocessor system to provide inventory control.

It is a still further object of the invention to provide a novel system in which reordering is triggered by information maintained in columns or other chromatographic components or environmental sampler components which wirelessly cooperate with databases recorded in a separate microprocessor.

It is a still further object of the invention to provide a quality control system in which the precision of characteristics such as retention times of columns is recorded on the component such as a column to enable automatic fitting of columns that have characteristics operating within predetermined ranges to applications requiring those predetermined ranges.

It is a still further object of the invention to provide a novel system for tracing the efficiency of certain chromatographic columns for pre-selected chemistries and runs or the times of runs.

It is a still further object of the invention to provide a novel system for automating combinatorial research using libraries of compounds accessed wirelessly by components of the system.

It is a still further object of the invention to provide a novel system for use in separation instruments such as chromatographs for recording data automatically in electronic notebooks.

It is a still further object of the invention to provide a system permitting on-line communication with security between chromatographic components and a central computer.

It is a still further object of the invention to provide a novel communication system for chromatographic and environmental apparatuses that is compatible with Wi-Fi or Bluetooth.

It is a still further object of the invention to provide a novel system for recording the characteristics of columns such as the column lining, the polar nature of solvents, the types of chromatography and the like.

It is a still further object of the invention to provide a novel system for recording information on chromatographic or environmental components useful in servicing the environmental or chromatographic components or identifying the end use or determining when the components are out of date.

It is a still further object of the invention to provide a system that renders chromatographic systems tamper proof in accordance with Part 11 of the Code of Federal Regulations.

It is a still further object of the invention to provide a novel system for recording all information needed to produce a drug in accordance with Part 9 of the Code of Federal Regulations.

It is a still further object of the invention to provide a novel system for transmitting billing information to a central station.

It is a still further object of the invention to provide a novel system for transmitting reliability information to a central system.

It is a still further object of the invention to provide information on columns for aiding and stacking the columns and avoiding mistakes such as information about proper length and types of columns for the stack.

It is a still further object of the invention to provide a novel column or other container that may sense characteristics such as temperature, conductivity, pH, pressure and the like with sensors built into a column and connected to a transmitter.

It is a still further object of the invention to provide a novel column, container or reactor that includes a sensor for sensing physical characteristics of a reactant, feedstock or fluid mixture and use the sensed characteristics for feedback.

It is a still further object of the invention to provide a novel system for identifying columns in a rack by triangulation, phase or the like.

It is a still further object of the invention to provide a novel system for transmitting data from one instrument to another.

It is a still further object of the invention to provide a novel system for recording specific information such as default conditions to customers or manufacturers.

It is a still further object of the invention to provide standard data such as good laboratory practice or good manufacturing practice on the components being manufactured.

It is a still further object of the invention to provide information useful for quality control for sorting columns by grade or cost or the like on a column.

It is a still further object of the invention to provide a novel system for recording steps in manufacturing or testing for quality control purposes.

It is a still further object of the invention to provide a novel system for recording flow rate, pressure, solvent mixture, pH, conductivity, dissolved oxygen, IQ, OQ, PQ and the like on a component of a separation system or environmental sampling system.

It is a still further object of the invention to provide a novel portable liquid chromatographic system with functions performed on the column in communication with external devices.

It is a still further object of the invention to provide recording-transmitting devices for communication with global positioning systems to record conditions at certain locations where a measurement is to be made by an environmental device.

It is a still further object of the invention to provide a novel system for tracking values of consumables such as solvent height in solvent containers in liquid chromatographic systems.

It is a still further object of the invention to provide stacking systems such as a scavenger column with separation columns.

In accordance with the above and further objects of the invention, a multiple fraction instrument includes at least one pumping system, at least one flow path, a flow path mounting fixture, a container mounting fixture adapted for receiving at least one container and a controller. The at least one pumping system has a first wireless communication device and the controller has a second wireless communication device. There is at least one other component of the multiple fraction instrument that has a third wireless communication device. The second wireless communication device is positioned to communicate wirelessly with at least the first and third wireless communication devices. Advantageously, at least one other analytical instrument is connected to receive a fraction from the flow path.

In this specification the words, "multiple fraction instrument or process" means instruments or processes used in scientific or investigative work such as in the separation sciences or environment studies that process multiple fractions or samples or component parts in a manner that requires identification or control of individual fractions or component parts or samples or the recall of information about individual ones of the fractions or component parts or samples. The words "wireless communication device" means a device that can either receive and/or transmit information wirelessly and may or may not have a non-volatile memory for storing information such as data or programs that can be transmitted, altered or sequenced or received. A wireless communication device may be either a transmitter, or a reader, a transceiver or any combination of these. In the preferred embodiment, they are RFID devices but may be Bluetooth or Wi-Fi or Zigbee or any other wireless system.

More specifically, a liquid chromatographic system includes at least one column, at least one column mounting fixture adapted for receiving the at least one column, at least one detector positioned to receive effluent from the at least one column, at least one controller, and at least one other component of a liquid chromatographic system. The at least one column has a first wireless communication device and at least one other component of a liquid chromatographic system has a second wireless communication device. The at least one controller has a third wireless communication device connected to communicate with the at least one controller and at least one of the first, second and third wireless communication devices is positioned to communicate with at least another of first, second and third wireless communication devices. There is at least one detector connected to a fourth wireless communication device and positioned to receive effluent from the column.

The fourth wireless communication device transmits information about detected species to the third wireless communication device. Moreover, a fraction collector and at least one collection vessel rack is positioned to receive effluent from the at least one detector and includes a fifth wireless communication device in communication with the fraction collector and at least a sixth wireless communication device in communication with one of the third and the fifth wireless communication devices. A personal computer has a wireless communication device that communicates with a wireless communication device on the at least one controller. The personal computer has an electronic notebook in memory and records customized data therein.

In the operation of the liquid chromatograph, data representing a chromatographic curve for a chromatographic column is recorded in a first wireless communication device attached to the chromatographic column. This curve is read when the chromatographic column is inserted into a column mounting fixture on a liquid chromatographic system. The data representing a chromatogram is received on a second wireless communication device communicating with a controller for the liquid chromatographic system. Data representing the sequence of solvent conditions for the chromatographic curve is transmitted from the second wireless communication device to a third wireless communication device communicating with a pumping system within the liquid chromatographic system. The data is used to pump the solvents to the chromatographic column in accordance with the sequence of solvent conditions transmitted to the third wireless communication device.

Data is wirelessly transmitted to the second wireless communication device from a fourth wireless communication device communicating with at least one detector positioned to receive effluent from the chromatographic column and data is transmitted from the second wireless communication device to a readout device to indicate peaks detected by the at least one detector and to a fraction collector to activate collection of bands. In another embodiment, there is a controller having a gradient program stored within it and a first wireless communication device electrically connected to and communicating with the controller to transmit information to a pumping system. The pumping system in a preferred embodiment includes at least two syringe pumps and at least two sources of liquid. The pumps may include at least one wireless communication device which receives data from a wireless communication device on the controller to control pumping rates. In the alternative, the chromatographic system may include at least one time proportioning electronically controllable liquid gradient switching valve and a second wireless communication device communicating with the at least one time proportioning electronically controllable liquid gradient switching valve.

The switching valve is connected to switch liquid flow from one or the other of the at least two sources of liquid to an inlet of at least one of the at least two syringe pumps. The first and second wireless communication devices are wired to transmit switching times of the at least one time proportioning electronically controllable liquid gradient switching valve to form gradient stored in the controller. One of the at least two syringe pumps is used for each one of multiple channels. Each of the at least two syringe pumps has a displacement of at least five milliliters and one of the at least two syringe pumps has a discharge outlet connected to a sample injection device and thence to a chromatographic column. The at least one wireless communication device includes a memory. The memory has data recorded in it representing a starting concentration of a solvent whereby the chromatographic system may separate a preselected component of a sample with the starting concentration of the solvent. The memory has data recorded in it representing a chromatographic curve with a starting concentration for purifying the preselected component of a sample and an ending point.

The instrument array may include a plurality of multiple fraction instruments, a general control system and at least some of a plurality of multiple fraction instruments. The multiple fraction instruments may include a corresponding one of a plurality of first wireless communication devices, the general control system includes a second wireless communication device and an input device for programming the computer. The second wireless communication device is positioned to communicate selectively or simultaneously with at least one of the plurality of the first wireless communication devices whereby the general control system may coordinate any of the plurality of multiple fraction instruments.

Advantageously, at least some of said multiple fraction instruments are liquid chromatographs and some are other types of instruments. The liquid chromatographs include columns having corresponding third wireless communication devices in communication with them. The third wireless communication devices include a nonvolatile memory having data indicating that the fractions collected are to be applied to other analytical instruments and instructions for the operations to be performed by the other analytical instruments. The other analytical instruments may be mass spectrometers for example.

Wireless communication devices connected to containers receiving fractions from the liquid chromatographs may include a nonvolatile memory having data indicating that the fractions collected are to be applied to other analytical instruments and instructions for the operations to be performed by the other analytical instruments. The other analytical instrument may be a mass spectrometer or any other instrument useful in further purifying or analyzing the output from the liquid chromatographs.

A chemical processor includes at least one reaction station having a reaction time controller, a controllable pipette or pump, a reactant vessel and a receptacle conveyor. The at least one reaction station includes at least a first wireless communication device and a plurality of receptacles. Each of the plurality of receptacles is connected to communicate with and is attached to one of a corresponding second wireless communication device. There is at least one analytical instrument that is connected to and communicates with a third wireless communication device and at least one transfer console for transferring materials from a receptacle to the at least one analytical instrument. At least some of the first, second and third wireless communication devices have a nonvolatile memory with data indicating at least one of the history of materials in the receptacle and instructions for processing the materials in the receptacle. The nonvolatile memory includes data indicating both the history of the materials in the receptacle and instructions for processing the materials in the receptacle.

In operation, a receptacle containing a material to be processed is moved to at least one reaction station where at least one of the steps of adding a reagent to the receptacle, heating the receptacle, delaying further action for a reaction time and agitating the material in the receptacle is performed. The materials and steps performed on the materials are recorded in a wireless communication device attached to the receptacle and processing instructions are recorded on the receptacle. The material is transferred to a second receptacle and the processing steps and materials are recorded on the second receptacle in a wireless device The materials are moved to an analytical instrument and a product of reaction may be separated into a third receptacle. The history of the process and the materials may be recorded on the third receptacle The steps and materials may be automatically logged into an electronic notebook.

A chromatographic column includes an inlet end having an inlet port, an outlet end having an outlet port, tubular side walls between the inlet end and the outlet end, at least one wireless communication device on at least one or more of the inlet end, outlet end or tubular side walls. The at least one wireless communication device may include a nonvolatile memory having data recorded on it and the data may include a precision of the column from run to run, data indicating a make and model of the column, a date of manufacture and a lot number of the column.

Another embodiment of chromatographic column includes an inlet end having an inlet port, an outlet end having an outlet port, tubular side walls between the inlet end and the outlet end, a sensor, at least one wireless communication device on at least one of the inlet end, outlet end and tubular side walls. The sensor communicates with one of a column and an environment near a column part and contents of the column and communicates with the at least one wireless communication device. The sensor and at least one wireless communication device includes a plurality of sensors each of which communicates with a corresponding one of a plurality of wireless communication devices. One of the plurality of sensors senses temperature and one of the plurality of sensors senses pH.

A chromatographic system includes at least one chromatographic column arrangement having a first column and a second column. The outlet of the first column communicates with the inlet port of the second column. There is at least one wireless communication device on at least one of the first column inlet end, first column outlet end and first column tubular side walls and at least one wireless communication device on at least one of the second column inlet end, second column outlet end and second column tubular side walls. The at least one wireless communication device on the first column includes a nonvolatile memory and the at least one wireless communication device on the second column includes a nonvolatile memory. With this arrangement, communication between the wireless communications devices may indicate to the controller an error in stacking the columns. Thus, an indication may be given to the user indicating a connection between the first and second columns is improper.

To control the inventory of component parts of a chromatographic system, a part of the chromatographic system includes a wireless communication device. Data is recorded on the wireless communication device indicating the number of parts of the chromatographic system that are available and data indicating the date of manufacture of the part. The date of manufacture of the part is periodically checked to reduce overall shelf time. Moreover, the inventory may be controlled by manufacturing the parts of the chromatographic system with a wireless communication device on them and recording a calibration curve in the wireless communication device so that the inventory may be broken down by quality and use of the parts. Moreover, the nonvolatile memory has data recorded on it and the data includes a precision of the column from run to run, data indicating the make and model of the column and a date of manufacture. This data may aid in controlling the selection of columns to be removed from inventory and where they should be shipped.

A chromatographic control system includes a plurality of component parts of the liquid chromatographic control system with at least one of the plurality of component parts having a selected characteristic recorded on a tag associated with the one component part. The tag is capable of transmitting information to a microprocessor. The microprocessor includes a memory containing a data base and the tag includes indicia that may be transmitted to the microprocessor. The microprocessor includes a receiver means for receiving the transmitted information and entering the information into the data base indicating a number of component parts having the selected characteristic. The data base may include an inventory target number recorded into it and multiple instruments.

One embodiment of an instrument management system includes a plurality of multiple fraction instruments and a general control system. At least some of the plurality of multiple fraction instruments includes a corresponding one of a plurality of first wireless communication devices. The general control system includes a second wireless communication device and a memory containing a data base. The data base includes data useful in managing a usage of at least some types of component parts of the plurality of the multiple fraction instruments. The data base includes data indicating a number of at least some types of component parts in the plurality of multiple fraction instruments, an average rate of usage of the types of components parts and a manufacturer's inventory of the type of component parts. The data base may include a model number, a price, and a source of a type of part whereby comparisons are made as to reliability of the type of part by manufacturer and make of the part. The database may include a rate of usage by individual customers whereby customers' needs can be forecast and used for management purposes to determine an inventory of the component parts needed and target inventory minimum and maximum and an actual number of the component parts on hand. The system provides an alert signal when either is exceeded.

In managing instrument systems, data may be transmitted from each of a plurality of multiple fraction instruments useful in managing usage of at least some types of component parts of the plurality of multiple fraction instruments to a wireless communication device connected to and in communication with a general control system. The communication may be from a plurality of wireless communication devices connected to and in communication with a corresponding one of the plurality of multiple fraction instruments. The data that is useful in managing the usage of at least some types of component parts of the plurality of multiple fraction instruments may be recorded in a data base within a memory of the general control system and the useful data may be used in managing the usage of at least some types of component parts of the plurality of multiple fraction instruments. The data base may include data indicating a number of at least some types of component parts in the plurality of multiple fraction instruments and an average rate of usage of the types of component parts and a manufacturer's inventory of the type of component parts.

For management purposes, the data base may include: (1) a model number, a price and a source of a type of part whereby comparisons are made as to reliability of the type of part by manufacturer; (2) the make and model number of the part; and (3) the rate of usage of components by individual customers whereby customer's needs can be forecast and used for management purposes. The rate of usage of components may be used to determine an inventory of the component parts needed. The data base may include target inventory minimum and maximum and an actual number of the component parts on hand. For example, the system provides an alert signal when either is exceeded. The data base may include new purchases by customers and increases and charges in materials, parts and processes to predict increases and decreases in purchases of the materials and parts using the information in the database.

A fraction collection system includes at least one container holder, a main frame and a microprocessor mounted to the main frame. The main frame includes a liquid receiving means adapted to be connected to communicate with a fluid outlet from a detector and is shaped and sized to receive at least one container holder in a container holder bed.

There is at least one distributor means in the fraction collector for moving a distributor outlet from container to container and communicating with the liquid receiving means, whereby fractions may be deposited in containers. The microprocessor communicates with a first wireless communication device and at least one container holder communicates with a second wireless communication device. The container holder bed includes a third wireless communication device and the second and third wireless communication devices transmit a signal to the third wireless communication device when the at least one container holder is positioned with respect to the at least one distributor means to receive liquid. The second wireless communication device includes a nonvolatile memory and the nonvolatile memory includes data identifying characteristics of the at least one container holder. The third wireless communication device includes a nonvolatile memory containing data identifying characteristics of the at least one container holder, wherein a signal may be sent to the first wireless communication device when data stored in the nonvolatile memories of the second and third wireless communication device matches.

The second wireless communication device identifies an end use to be made of the at least one container holder. A valve that is automatically switchable to direct liquid to either the at least one distributor means or to waste communicates with a fourth wireless communication device wherein the first wireless communication device transmits a signal to the fourth wireless communication device to switch the liquid from flowing to the at least one distributor means or flowing into waste when a peak is over.

The fraction collection system may also include at least one container holder, a main frame and a microprocessor mounted to the main frame. The main frame includes a liquid receiving means adapted to be connected to communicate with a fluid outlet from a detector and is shaped and sized to receive the at least one container holder in a container holder bed. There is at least one distributor means for moving a distributor outlet from container to container and communicating with the liquid receiving means, whereby fractions may be deposited in containers. The microprocessor communicates with a first wireless communication device. There is at least one container in the container holder and the at least one container holder communicates with a second wireless communication device. The container holder bed includes a third wireless communication device and the second and third wireless communication devices transmits a signal to the third wireless communication device when the at least one container holder is positioned with respect to the at least one distributor means to receive liquid.

To collect fractions, an identification of at least one container holder is sent when the at least one container holder is in position to receive liquid from a distributor of a fraction collector to a controller. Liquid is inserted into containers in the at least one container holder upon receiving the identification of the at least one container holder in position to receive the liquid and insertion is inhibited when the at least one container holder is not in the proper position. The second wireless communication device identifies characteristics of the at least one container holder. The third wireless communication device supplies data identifying characteristics of the at least one container holder, wherein a signal may be sent to a first wireless communication device when data stored in nonvolatile memories of the second and third wireless communication device matches.

The third wireless communication device supplies data identifying an end use of the at least one container holder. The at least one container holder may be used in another instrument as indicated by data recorded on the at least one container holder. The wireless communication device associated with a rack, or micro titer plate or other holder of containers for the fraction collector may include a map of the containers such as for example X and Y coordinates. This may be used to center a distributor arm over the container or for a user or robot to locate a particular container with a selected fraction.

The liquid sampler includes a pump for repeatedly drawing liquid from a body of liquid, at least one container, at least one container mounting fixture adapted for receiving at least one container, at least one controller and a movable fixture for providing at least one flow path. The pump has a first wireless communication device and the at least one controller has a second wireless communication device. The at least one controller communicates with the pump through the first and second wireless communication devices and includes a program for initiating pumping and determining a container into which at least one sample is deposited. The third wireless communication device is positioned to communicate wirelessly with at least the first wireless communication device and the second wireless communication device. Container stations are connected to communicate with wireless communication devices to identify the container station wherein the at least one controller may direct fluid to that container station.

To collect and analyze environmental samples, an instrument includes at least one pumping system programmed to repeatedly draw liquid from a body of liquid, a plurality of containers and at least a corresponding one of a plurality of consoles for each pumping system. Each of the plurality of consoles has a station for at least a corresponding one of the plurality of containers. A corresponding one of a plurality of container mounting fixtures is provided to receive at last one column.

There is at least one corresponding controller for each of the plurality of consoles and at least a corresponding one of a plurality of movable fixtures for providing at least one flow path in each of the plurality of consoles. The corresponding controller communicates with at least one pump and includes a program for initiating pumping and determining a container into which at least one sample is deposited. Each of the pumps has a corresponding one of a plurality of first wireless communication devices. The at least one corresponding controller has a second wireless communication device and a third wireless communication device. The third wireless communication device is positioned to communicate wirelessly with at least the first wireless communication device in at least a corresponding one of a plurality of consoles and the second wireless communication device.

In this liquid sampler, container stations are connected to communicate with wireless communication devices to identify the container station wherein the at least one corresponding controller may direct fluid to that container station. An analyzing station includes a wireless communication device wherein the analyzing station may identify a source of each of the plurality of containers.

To provide environmental sampling on site, liquid is pumped from a body of liquid into at least one container within a corresponding one of a plurality of container mounting fixtures adapted to receive at least one container. A flow path is moved over selected containers and pumping action is initiated. The flow path is moved over the selected containers under the control of a first wireless control device connected for communication with a control system and a second wireless control device communicates with the movable fixture. The controller has a second wireless communication device and a third wireless communication device. The third wireless communication device is positioned to communicate wirelessly with at least the first wireless communication device and the second wireless communication device. The container stations are connected to communicate with wireless communication devices to identify the container station wherein the controller may direct fluid to that container station through the wireless communication devices.

A portable instrument has a chromatographic column with sensors spaced along its length. The sensors are connected to communicate with wireless communication devices. The portable instrument has an input and a readout device connected to a wireless communication device wherein readings from said sensors may be displayed. The portable instrument includes wireless communication devices that may communicate remotely with other instruments. The portable instrument may include a GPS to provide location and the location may be recorded on the containers having the sample in them. To environmentally test samples in the field, a portable instrument containing wireless communication devices measures samples and records the measurements on the wireless communication devices. It may then transfer the measurements wirelessly from the wireless communication device to other instruments.

BRIEF DESCRIPTION OF THE DRAWINGS

The above noted and other features of the invention will be better understood from the detailed description when considered in connection with the following drawings, in which:

FIG. 12 is a block diagram of a waste water sampling system in accordance with an embodiment of the invention; and FIG. 13 is a block diagram of an environment sampling system in accordance with an embodiment of the invention.

DETAILED DESCRIPTION

Figure 1:
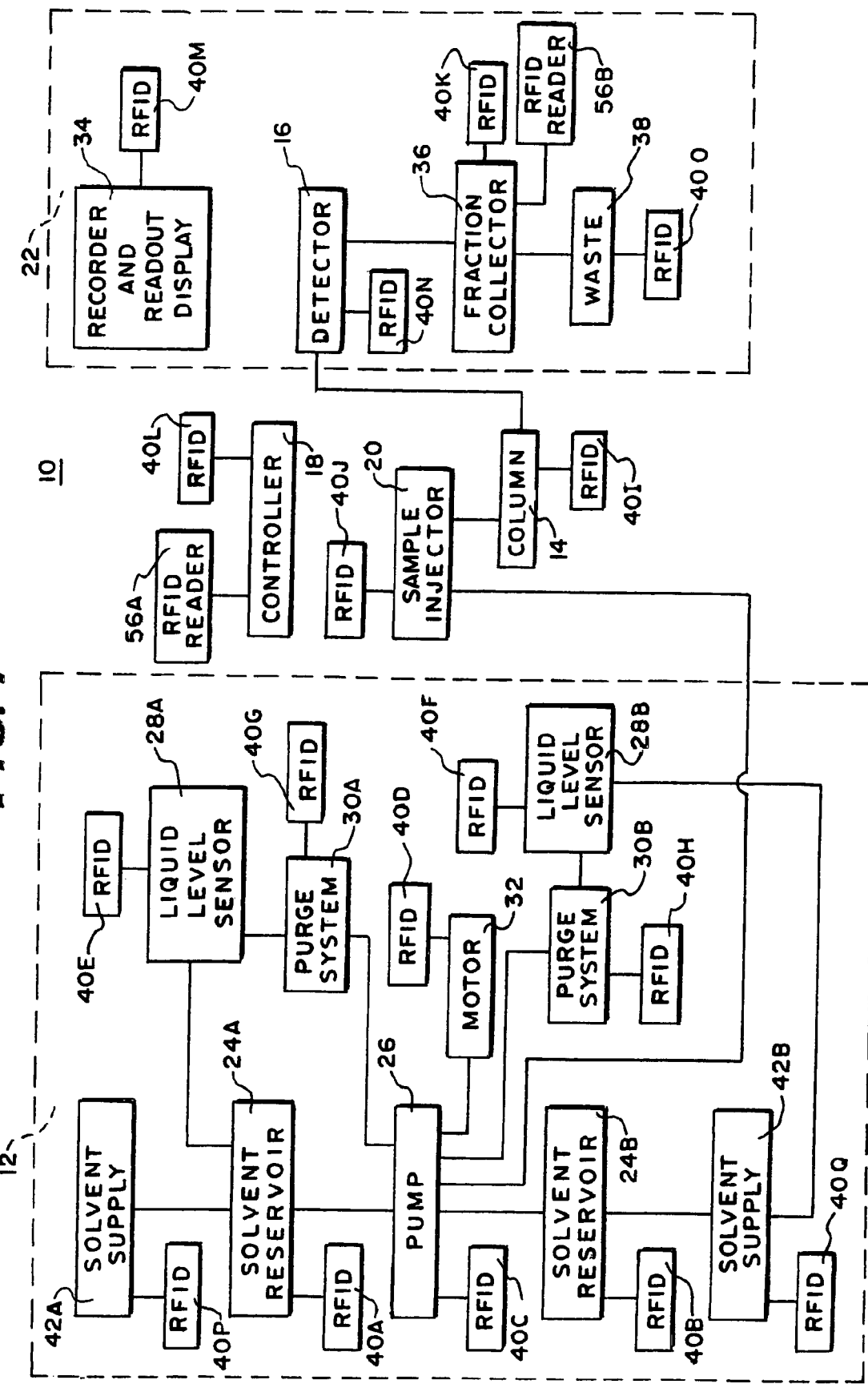
FIG. 1 is a block diagram of liquid chromatographic system in accordance with an embodiment of the invention.

In FIG. 1, there is shown a block diagram of a liquid chromatographic system 10 having a pumping system 12, a controller 18, at least one chromatographic column 14, a sample injector 20, a detector 16, and a collection system 22. In the preferred embodiment, an array of columns, detectors, sample collectors, pumps and pump motors would be utilized as described more completely in U.S. Pat. No. 6,427,526 granted Aug. 6, 2002, to Davison, et al., but the invention is equally applicable to any chromatographic system including the single column system shown in FIG. 1 and any other multiple fraction instrument such as environmental waste water collection systems. In this specification, "multiple fraction instruments" shall mean instruments used in scientific or investigative work such as in the separation sciences or environmental studies that process multiple fractions or samples or component parts in a manner that benefits from identification or control of the individual fractions, samples or component parts or the recall of information about individual ones of the fractions or samples or component parts.

The pumping system 12 in the embodiment of FIG. 1 includes first and second solvent reservoirs 24A and 24B, at least one pump 26 driven by at least one pump motor 32, liquid level sensors 28A and 28B communicating with the solvent reservoirs 24A and 24B respectively and purge systems 30A and 30B. The pumping system 12 supplies solvent to the column 14 and detector 16 or in the case of a preparatory liquid chromatographic system utilizing an array of columns and detectors, to the arrays of columns and detectors. The supply of solvent is under the control of the controller 18. The purge systems 30A and 30B communicates with the pump or pumps 26 to purge the pumps and the lines between the pumps and the column between chromatographic runs. The pump or pumps 26 supply solvent to the column or columns or to the detector or detectors 16 under the control of the controller 18.

The controller 18 receives signals from the detector or detectors 16 indicating bands of solute and activates a fraction collector 36 and readout display 34 in a manner known in the art. One suitable fraction collection system is the FOXY® 200 fraction collector available from Teledyne Isco, Inc., 4700 Superior Street, Lincoln, Nebr. 68504.

To supply solvent to the pump or plurality of pumps 26, the pumping system 12 includes a plurality of solvent reservoirs such as the reservoirs 24A and 24B. In the case in which a plurality of pumps are utilized, the solvent reservoirs will communicate with the pumps 26 through a manifold that channels solvent to each of the pumps 26. Each of the pumps may also include a separate motor or one motor may drive pistons from the plurality of pumps such as the motor or plurality of motors 32. In some embodiments, there will be a purge system such as the purge systems 30A and 30B for purging the pump or pumps 26 and the connecting conduits. In the preferred embodiment, the solvent reservoirs 24A and 24B communicate with corresponding liquid level sensors 28A and 28B that sense the amount of solvent in the reservoirs 24A and 24B so that the reservoirs may continue to have solvent while the system is operating.

The column or columns 14 and detector or detectors 16 receive the solvent from the pumping system 12 in a manner known in the art. The sample injector 20 injects sample into the column 14 so that the solvent system may separate the components of the sample and carry them through the detector 16 and to the analysis and collection system 22.

The analysis and collection system 22 includes the fraction collector 36, the detector 16 and the readout display 34. The fraction collector 36 collects solute from the column or columns 14 and permits unselected material to flow through a waste system 38. The detector 16 also receives the solute and applies signals to the controller 18, which in turn controls the fraction collector 36 and the readout display 34 to provide signals indicating the separate species to be collected by the fraction collector 36 and to provide a read out to the user.

At least some of the solvent reservoirs 24A and 24B, purge systems 30A and 30B, liquid level sensors 28A and 28B, pumps 26, pump motors 32, controllers 18, sample injectors 20, columns 14, detectors 16, readout display or displays 34 and fraction collectors 36 include one or more RFID devices. While in FIG. 1, the liquid chromatographic system has these components hardwired together, each of these components may communicate through a separate one of RFID devices 40A-40Q.

In operating the chromatographic system 10 or similar chromatographic systems using wireless transmitters as a substitute for hardwiring between at least some of the components, a controller 18 supplies packets of data to the RFID 40L and the RFID 40L transmits the data to other units or receives data and transmits it to the controller 18. For example, in a gradient run, the solvent reservoir 24A is connected to the RFID 40A and the solvent reservoir 24B is connected to the RFID 40B. With this arrangement, the RFID 40A identifies the solvent within the solvent reservoir 24A and the RFID 40B identifies the solvent within the solvent reservoir 24B.

During the chromatographic run, the controller 18 supplies gradient information to the RFID 40L which transmits to the RFID 40D to operate the motor or motors 32. They in turn operate the pumps 26 to pump solvent from the solvent reservoirs 24A and 24B. The pumps RFID 40C may provide feedback information by delivering packets of information concerning the pumping from their respective reservoirs to the RFID's 40A and 40B, which in turn transmits the information to the controller 18 to which it is connected. In this way, the controller 18 through packets of data may control the gradient as it is pumped through the column 14. At the beginning of a gradient run, the controller 18 may transmit data to the RFID 40L which in turn may transmit data to the RFID 40J to initiate the injection of a sample from the sample injector 20 into the column 14. In the case of preparatory chromatography, the column 14 may contain in the RFID device 40I that cooperates with it a chromatogram to supply information to the controller 18 by transmitting packets of information from the RFID 40I connected to the column 14 to the RFID 40L connected to the controller 18. This information may enable the controller 18 to transmit information from its RFID 40L to the RFID 40D for the pump motors 32 and the pump or pumps 26 through their respective RFID to pump the desired solvent concentration for the preparatory purification. If the solvent runs low in one of the solvent reservoirs 24A or 24B, the liquid level sensors 28A and 28B supply this information to their respective RFID devices 40E and 40F which may transmit information to the appropriate one of solvent supplies 42A and 42B to replenish the supply of the solvent in the solvent reservoirs 24A and 24B.

During the chromatographic run, the controller 18 receives information from the detector 16. This information may be transmitted by the RFID 40N connected to the detector 16 to the RFID 40L connected to the controller 18. The controller 18 may in turn transmit this information to the read out display 34 by supplying the information to its RFID 40L which may transmit it wirelessly to the RFID 40M which in turn may supply it to the read out 34. Similarly, the detector 16 may transmit information from its RFID 40N to the RFID 40K connected to the fraction collector 36 to activate the fraction collector 36 to collect peaks detected by the detector 16. Moreover, the RFID 40N connected to the detector 16 may supply this information to the controller 18 through its RFID 40L. The controller 18 may in turn supply information through its RFID 40L to the RFID 40K on the fraction collector 36 to control the positioning of collecting containers with respect to the inlet to the fraction collector 36 so as to supply bands to predetermined containers and follow a pattern that may be stored in the controller 18 if desired. A RFID reader 56B may read RFIDs on racks or other collector container holders and provide signals to the controller indicating proper registration of the proper rack or information about which location in a rack is to receive a fraction.

In one embodiment, the RFID 40I connected to the column 14 may indicate the past history of the column. Prior to a chromatographic run, this information may be obtained by the controller 18 by transmitting a request for it from its RFID 40L. The program and the controller 18 may compare this information with the identification of the solvents obtained from the RFID 40A associated with the solvent reservoir 24A and the RFID 40B associated with the solvent reservoir 24B. If use of the column indicates the new solvent conditions are not appropriate for use in the column, the controller 18 may terminate the chromatographic run and display a notice on the readout display 34 by transmitting signals from the RFID 40L associated with the controller 18 to the RFID 40D associated with the motor 32 and the RFID 40M associated with the readout display 34. The fraction collector 36 may also communicate through its RFID 40K with the controller 18. This communication together with the communication from the column 14 and the detector 16 with the controller 18 may insure that racks or individual containers are properly positioned prior to depositing effluent from the column into the containers under the control of the detector 16.

While in the preferred embodiment, the individual components of the liquid chromatographic system 10 such as the detector 16, pumps 26, solvent reservoirs 24A and 24B and the like communicate directly with the controller 18 which may in return send signals to other units such as the readout display 34, other communication paths may be used. In the preferred embodiment, the center of communication is the wireless communication device 40L that communicates with the controller 18, which has substantial memory in it. Therefore, it is possible, for example, for the detector 16 to communicate directly with the readout display 34 to display peaks rather than transmitting the peaks to the controller 18 through the wireless communication device 40L and having the wireless communication device 40L transmit the peaks to the readout display 34 and fraction collector 36 through their respective wireless communication devices 40M and 40K.

Figure 2:
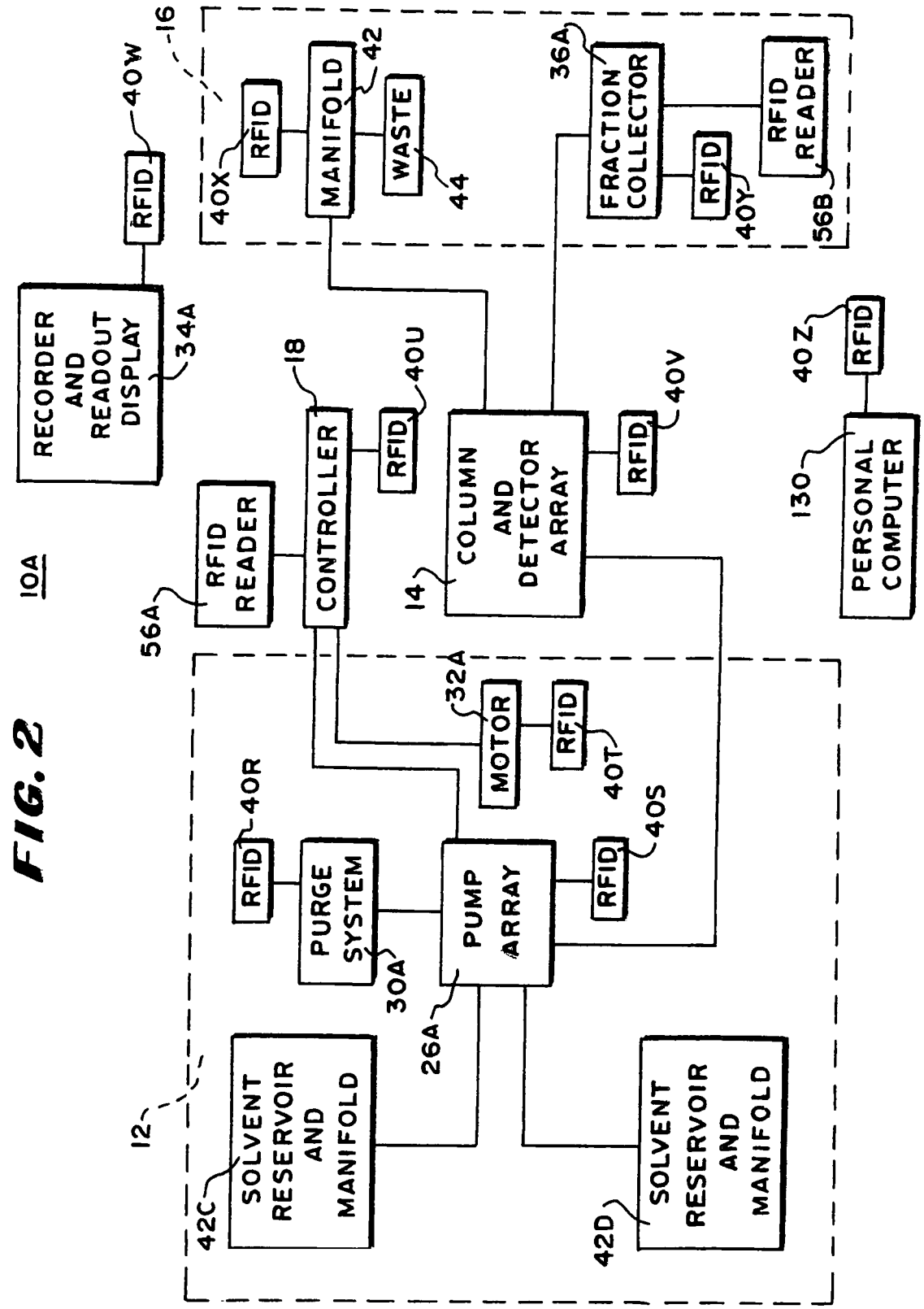
FIG. 2 is a block diagram of a preparatory liquid chromatographic system in accordance with another embodiment of the invention.

In FIG. 2, there is shown a block diagram of a preparatory liquid chromatographic system 10A having a pumping system 12, a column and detector array 14A, a collector system 16, a controller 18, a purge system 30A and a personal computer 130. The personal computer 130 communicates with a wireless communication device 40Z. The pumping system 12 applies solvent to the column and detector array 14 under the control of the controller 18. The controller 18 supplies signals to a motor 32A which drives a pump array 26A by wirelessly transmitting signals from the RFID 40U electrically connected for communication with the controller 18 to the RFID 40T electrically connected for communication with the motor 32A. The movement of the pump array 26A provides a signal to the RFID 40S connected to it which transmits the signals in return to the RFID 40U so that a jam or interruption is sensed and the controller 18 receives a feedback signal indicating proper movement of the pump array 26A to pump liquid from solvent reservoir and manifolds 42C and 42D to the column and detector array 14 from which a fluid flows into the collector system 16 under the control of the controller 18. Signals from the detectors in the column and detector array 14 are transmitted by the RFID 40V to the RFID 40U that communicates with the controller 18. The controller 18 in turn sends signals reflecting the detection of bands to a readout display 34A by transmitting them wirelessly to the wireless communication device 40W that communicates with the readout display 34A. Signals transmitted by the wireless communication device 40U from the controller 18 are also received by the wireless communication device 40Y that communicates with a fraction collector 36A to collect samples in a manner known in the art. A suitable fraction collector system is the FOXY® 200 fraction collector available from Teledyne Isco, Inc., 4700 Superior Street, Lincoln, Nebr. 68504. The chromatographic system shown in FIG. 2 and described herein is also described without the wireless system in U.S. Pat. No. 6,427,526 the disclosure of which is incorporated herein by reference.

To supply solvent to the pump array 26A, the pumping system 12 includes a plurality of solvent reservoirs and manifolds, a first and second of which are indicated at 42C and 42D respectively, a pump array 26A and a motor 32A which is driven under the control of the controller 18 to operate the array of pumps 26A in a manner to be described hereinafter. The controller 18 also controls valves in the pump array 26A through the wireless communication device 40S to control the flow of solvent and the formation of gradients as the motor 32A actuates the pistons of the reciprocating pumps in the pump array 26A simultaneously to pump solvent from a plurality of pumps in the pump array 26A and to draw solvent from the solvent reservoirs and manifolds such as 42C and 42D.

During this pumping process, a pump piston may become jammed. If a pump in the pump array 26A should become jammed, there is an automatic release mechanism for releasing the pressure from at least that one pump to avoid damage. In the preferred embodiment, the release mechanism is a fluid pressure release mechanism for that pump set at a value above the rated pressure such as at 170 psi so that the motor 32A may continuously move the pistons up and down without damage. Moreover, valves in the pump array 26A control the amount of liquid, if any, and the proportions of liquids from different reservoirs in the case of gradient operation that are drawn into the pump and pumped from it. The manifolds communicate with the reservoirs so that a plurality of each of the solvents such as the first and second solvents in the solvent reservoir manifolds 42C and 42D respectively can be drawn into the pump array 26A to permit a simultaneous operation of a number of pumps.

While in the preferred embodiment, an array of reciprocating piston pumps are used, any type of pump is suitable whether reciprocating or not and whether piston or not. A large number of different pumps and pumping principles are known in the art and to persons of ordinary skill in the art and any such known pump or pumping principle may be adaptable to the invention disclosed herein with routine engineering, and in most cases, one motor drives a plurality of pumps. While two solvents are disclosed in the embodiment of FIG. 2, only one solvent may be used or more than two solvents may be used. Because of the operation of a plurality of pumps simultaneously driven by a single motor, efficiency and cost reduction are obtained by this pumping mechanism.

To process the effluent, the collector system 16 includes a fraction collector 36A to collect solute, a manifold 42 and a waste depository 44 to handle waste from the manifold 42. One or more fraction collectors 36A communicate with the column and detector array 14 to receive the solute from the columns either with a manifold or not. A manifold may be used to combine solute from more than one column and deposit them together in a single receptacle or each column may deposit solute in its own receptacle or some of the columns each may deposit solute in its own corresponding receptacle and others may combine solute in the same receptacles. The manifold 42 communicates with the column and detector array 14 to channel effluent from each column and deposit it into the waste depository 44. The fraction collector 36A may be any suitable fraction collector such as that disclosed in U.S. Pat. No. 3,418,084 or the above-identified FOXY® fraction collector.

The wireless communication device 40U in the preferred embodiment transmits information to the wireless communication device 40Z which records the information in an electronic notebook stored in the memory of the personal computer 130 in a manner known in the art. There are many electronic notebook systems and they have formatting as part of the program. For example, Waters Laboratory Informatics notebook will log all operations performed and prepare customized reports.

Figure 3:
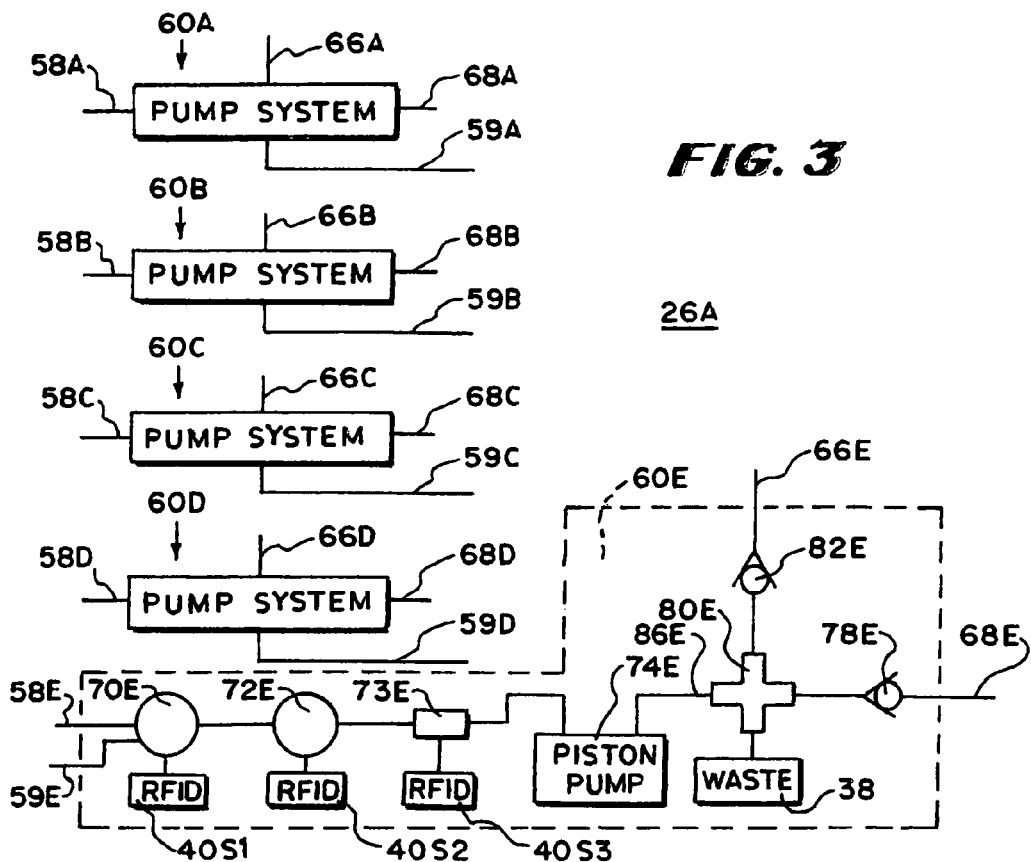
FIG. 3 is a schematic block diagram of a pump array in accordance with an embodiment of the invention.

In FIG. 3, there is shown a schematic block diagram of a pump array 26A having a plurality of piston pump systems 60A-60J (piston pump systems 60A-60E being shown for illustration in FIG. 3) although in the preferred embodiment there are ten such pumps each arranged to communicate with corresponding ones of ten outlets from the manifolds of the solvent reservoir and manifolds 42C and 42D (FIG. 2) to pump solvent from the reservoirs and manifolds 42C and 42D into corresponding ones of the columns (not shown in FIG. 3). In FIG. 3, four of the pump systems 60A-60D are shown in block form and a fifth pump system 60E is shown in greater detail with the understanding that each of the ten pump systems are substantially identical so that the explanation of the pump system 60E is an adequate explanation of all of the pump systems.

Each of the pump systems communicates with a corresponding one of manifold outlets 58A-58J (58A-58E being shown in FIG. 3) and 59A-59J (59A-59E being shown in FIG. 3) to receive two different solvents for the purpose of forming a gradient. They may also communicate with a source of purge fluid as indicated by purge conduits 66A-66J (66A-66E being shown in FIG. 3). With this arrangement, each of the pumps draws solvent into it from the solvent reservoirs in the solvent reservoirs and manifolds 42C and 42D (FIG. 2). The solvent flows from the pumps through a corresponding one of outlets 68A -68J (68A-68E being shown in FIG. 3).

The pump system 66E includes an inlet conduit 58E from the first solvent reservoir and manifold 40 (FIG. 2), the inlet conduit 59E from the second solvent reservoir and manifold 52, a three-way solenoid valve 70E, a two-way solenoid valve 72E, and long flow conduit 73E, a reciprocating piston pump 74E and a check valve 78E. With this arrangement, the two different solvents from the conduits 58E and 59E are applied to the pump 74E through a common point connecting the three-way solvent valve 70E and the two-way solvent valve 72E. In the preferred embodiment, two cycles of solvent are applied for each stroke of the piston pump 74E. The size of the cylinder, the size of the flow conduit 73E, the speed of the refill and delivery strokes of the piston are selected to ensure mixing within the pump 74E and flow conduit 73E so as to pump a formed gradient through a conduit 86E, through the check valve 78E and an outlet conduit 68E to the column and collector array 14 (FIG. 2). For this purpose, the pump cylinders are in the range of one inch to eight inches long. In the preferred embodiment, the cylinders are 3.5 inches long.

To provide two injections or charges of solvent during a refill portion of a pump cycle, the two-way electronically controlled solvent valve 72E opens once during each piston refill stroke of the pump 74E under the control of a signal received from wireless communication device 40S2 which receives a signal wirelessly from the wireless communication device 40U (FIG. 2) that communicates with the controller 18 (FIG. 2). Enclosures join the delivery portion of the pump cycle. In the preferred embodiment, the two-way valve 72E is a solenoid valve. To provide a gradient, the three-way electronically-control proportioning valve 70E switches between the two solvent reservoirs several times during each refill stroke in response to a signal from the wireless communication device 40S1 in communication with it. The wireless communication device 40S1 receives a signal for this purpose from the controller 18 by wireless transmission from the wireless communication device 40U (FIG. 2) to open to the first solvent reservoir and manifold 42C and then to the second solvent reservoir and manifold 43D (FIG. 2) to provide both solvents in two stages for better mixing. The proportion of the time the three-way valve 70E is open to the first solvent reservoir and manifold 42C and then to the second solvent reservoir and manifold 42D determines the composition of the mixture in the gradient. Both of the solenoid operated valves 70E and 72E are under the control of the controller 18 to which they electronically communicate through wireless communication devices.

Figure 4:
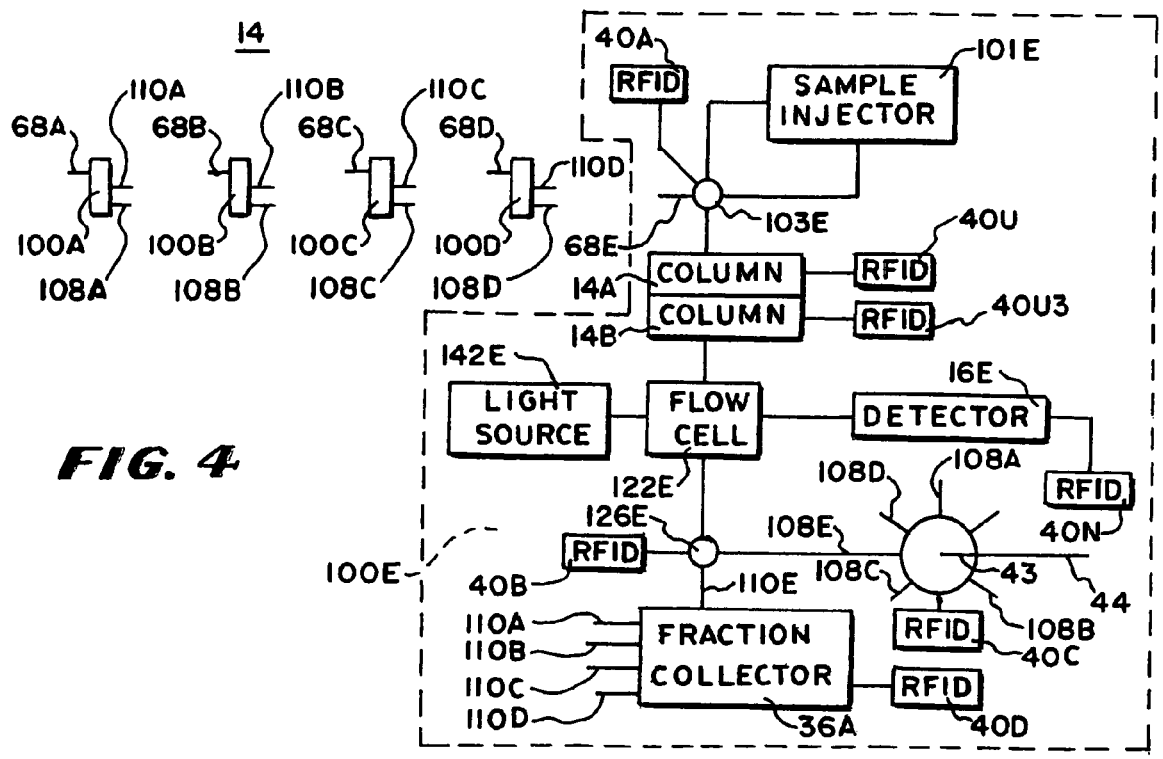
FIG. 4 is schematic diagram of a column and detector array forming part of the embodiment of FIG. 3.

In FIG. 4, there is shown a schematic diagram of a column and detector array 14 having a plurality of columns and detectors, five of which are indicated as 100A-100E, a corresponding plurality of outlet conductors 68A-68E, a corresponding plurality of solute outlets 110-110E, a corresponding plurality of waste outlets 108A-108E from the manifold 42 (FIG. 2) and a fraction collector 36A. In the preferred embodiment, there are ten columns and detectors. For illustration, the columns and detectors 100A-100D are shown as a general block whereas the column and detector 100E is shown in greater detail with the understanding that the columns and detectors 100A-100D are substantially the same. Moreover, while five columns and detectors are shown to correspond with the example being used in this application, more or less could readily be used and ten are used in the preferred embodiment.

The column and detector 100E includes an injector system 102E, a column stack 14A and 14B in the column and detector array 14, a detector 16E in the column and detector array 14, a waste outlet 108E and the solute outlet 110E. With this arrangement, solvent, whether a gradient or not, flows in the conduit 68E through the injector 110E, through the column stack 14A and 14B within the column and detector array 14, a flow cell 122E, where solute may be detected and from there into the collection system 16 (FIG. 2) for the collection of solute and the disposal of waste. The column stack (14A and 14B in FIG. 4) may instead be any type of chromatographic column regardless of the mode of operation and it is generally packed in accordance with the separation problem. In the preferred embodiment, the column is REDISEP DISPOSABLE COLUMNS sold by Teledyne Isco, Inc., 4700 Superior Street, Lincoln, Nebr. 68504. It is mounted to either receive a sample injection manually from a syringe or automatically from the injector 101E as well as receiving solvent on the outlet 68E. Its outlet flows through the detector system in the column and detector array 14.

In FIG. 4, the stack of columns 14A and 14B are shown for illustration. The outlet of the column 14A communicates with the inlet of the column 14B in a manner known in the art so that the inlet port of the column 14A receives solvent and sample from a valve 103E and the outlet port of the column 14B is delivered to the flow cell 122E. In this arrangement, the wireless communication device 40U is connected to communicate with the column 14A and the wireless communication device 40U3 is connected to communicate with the column 14B. These wireless communication devices each contain information about their characteristics so that a reader and microprocessor may compare the information and determine if the connection is correct or not and convey this information appropriately to the user such as through a display or alarm or inhibiting the operation of the pumps through the controller. For example, there may be recorded on the wireless communication devices associated with the columns: (1) the past history complete enough to avoid incompatible solvent systems by having the microprocessor with which it communicates indicate the incompatible use; (2) a sample chromatographic curve for use by the chromatographer; (3) a calibration curve; (4) the precision or an indication of the precision of the column construction which may be used to grade the column so that better grade columns may be sold to higher price markets; (5) flow rates; (6) pressures; (7) solvent mixtures; (8) pH; (9) conductivity; (10) dissolved oxygen and the like. The efficiency of the column with certain chemistries or processes can be determined and recorded.

At the start of the chromatographic run, the wireless communication device 40J (FIG. 1) receives a signal from the wireless communication device 40U (FIG. 2) that communicates with the controller 18 and in turn switches the valve 103E so that solvent flows into the injector 101E and from the injector through the column (14A, 14B) and into the flow cell 122E for detection of bands.

The detection system includes a light source 142E, the flow cell 122E, a detector 16E and a valve 126E for channeling fluid either to the waste outlet 108E through the conduit 44 or to the collector outlet 110E. The light source 142E, hereinafter referred to as the optical bench, applies light from a source common to each of the column and detector assemblies 100A-100E and applies it through each of the corresponding ones of the flow cells including the flow cell 122E and from there to the corresponding detectors including the detector 16E. The signal received indicates the effluent to be channeled to the collector 36A and that to be channeled to the waste for the particular column and detector system.

The injector 102E includes a solid sample load cartridge in the preferred embodiment and a four-way manual selective valve 103E for controlling the selection of sample and injection into the columns 14A and 14B. In the embodiment of FIG. 4, an individual injector system (injector system 102E being shown in FIG. 4) is provided for each of the columns although the outlet from one injector could go to a manifold to supply the same sample to a plurality of columns and/or the outlet from one injection cartridge could go to a plurality of injection valves if desired. Similarly, a single function collector 36 is shown but a plurality of such collectors could be used with the individual valves connected to more than one collector.

The injector system 102E includes the four-way valve 103E for alternately injecting sample from the sample injector 110E, which in the preferred embodiment is a cartridge, and selecting the solvent gradient from the outlet 68E from the pumping system. Thus a sample may be injected and then by turning the manual valve 103E, the chromatographic run may be initiated. While a manual four-way valve 103E is shown, automatic injector valves are also available and may be utilized.

Figure 5:
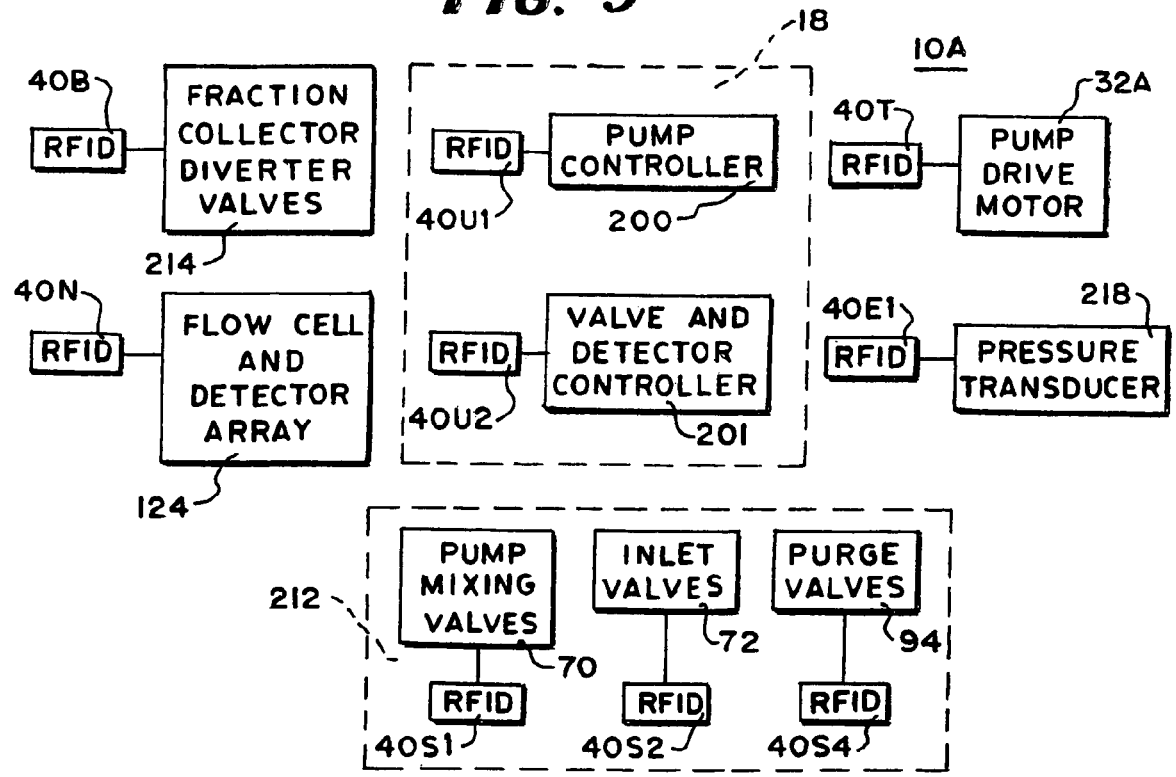
FIG. 5 is a block diagram of a chromatographic system in accordance with an embodiment of the invention.

In FIG. 5, there is shown a block diagram of the chromatographic system 10A having fraction collector diverter valves 214, a flow cell and detector array 124, the controller 18, a pressure transducer 218 and a valve array 212 for pumping solvents. This block diagram illustrates the connections through wireless communication devices between for example the controller 18, a pump drive motor 32A, the fraction collector diverter valves 214, the column and detector array 14 and the valve array 212. As shown in FIG. 5, the controller 18 includes inter alia functional components such as the pump controller 200 and the valve and detector controller 201. The valve array 212 includes the pump mixing valves 70, the inlet valves 72 and the purge valves 94.

As shown in FIG. 5, the pump controller 200 is connected to the series pump drive 32A and a pressure transducer 218 in a feed-back arrangement such as that described in U.S. Pat. No. 5,360,320, the disclosure of which is incorporated herein by reference. Specifically, the feed-back circuit disclosed in connection with FIGS. 8 and 9 in columns 11, 12, 13 and 14 of U.S. Pat. No. 5,360,320 for controlling the pump disclosed in FIG. 4 of that patent is utilized here. The pump controller 200 also interacts with the valve and detector controller 201 to control the flow and detector array 124 and the fraction collector diverter valves 214 for the fraction collector 36A (FIG. 4). The valve and detector controller 201 supplies signals to control mixing valves 70A-70J (shown collectively at 70), the inlet valves 72A-72J (shown collectively at 72) and the purge valves 94 of the valve array 212. With this arrangement, the detection of bands to be collected controls the fraction collector valves to channel the collection into the appropriate containers.

This system operates as described in U.S. Pat. No. 6,427,526 except instead of hard wiring between the units, wireless communication devices transmit data or packets of data to control the operations thereof.

Figure 6:
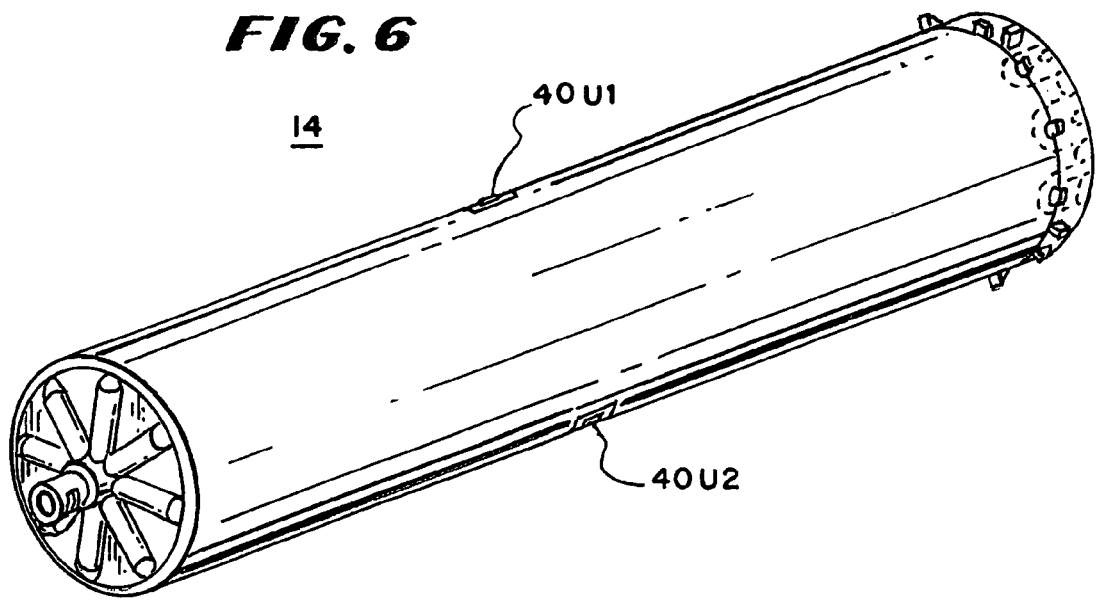
FIG. 6 is a simplified perspective view of a column having a wireless communication device communicating with it.

In FIG. 6, there is shown a simplified perspective view of a column 14 having a first wireless communication device 40U1 and a second wireless communication device 40U2 positioned 180 degrees from each other. In FIG. 1, they are shown mid-section of the column but may be positioned anywhere in the column where they will be in reasonably close communication with a wireless receiver. By positioning them 180 degrees apart, the column becomes insensitive to the rotational orientation since one or the other of the wireless communication devices will have an unobstructed communication path to a receiver mounted on the casing of the chromatographic system.

Figure 7:
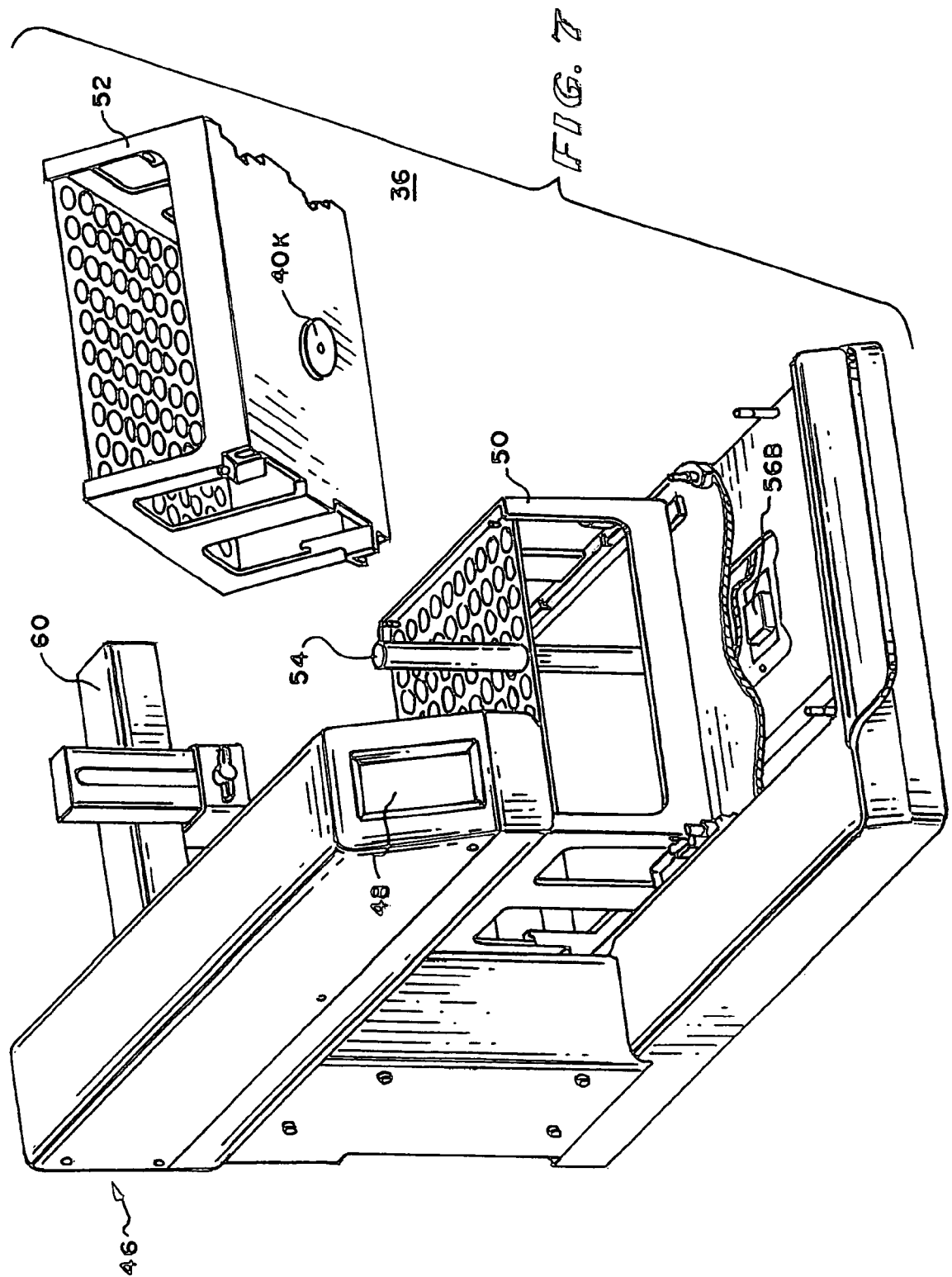
FIG. 7 is a perspective view of a fraction collector in accordance with an embodiment of the invention.

In FIG. 7, there is shown a perspective view of a fraction collector 36 including a main frame 46 and a plurality of racks such as a first test tube rack 50 and a second test tube rack 52 exploded away and turned to show its bottom side. The main frame includes a touch screen or LCD display 48, a distributor arm 60, an RFID reader 56B, a wireless communication device 40K. Each of the test tube racks has a wireless communication device 40K, which in the preferred embodiment is an RFID device mounted to its bottom side where it may come in proximity to a reader such as the RFID reader 56B. The readers and wireless communication devices determine if a rack is in position and may identify the rack such as by the number of openings and cross section so as to provide proper identification for the distributor arm 60 to move into position and distribute fluid into the appropriate tubes such as the test tube 54. In the embodiment of FIG. 7, a fraction collector 36 with two different racks 50 and 52 is shown, one of which is exploded away but each of which may be moved automatically into position where the registration and type may be checked. The information may then be transmitted to the microprocessor associated with the fraction collector 36 to distribute liquids appropriately.

Figure 8:
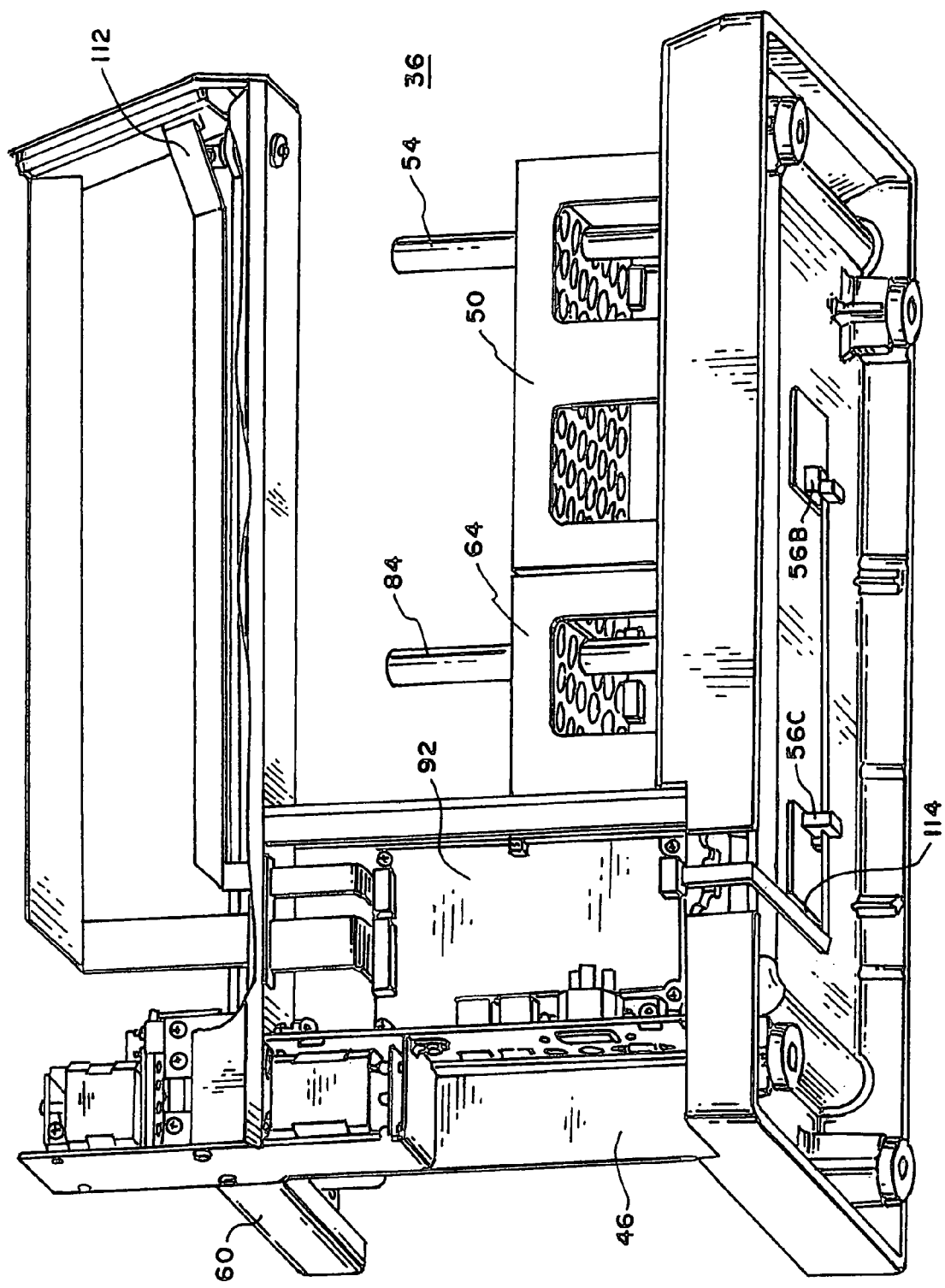
FIG. 8 is a perspective view of the fraction collector of FIG. 7 shown from another angle.

In FIG. 8, there is shown a perspective view of the fraction collector 36 viewed from the bottom and back side showing the distributor arm 60, the main frame 46, RFID readers 56B and 56C connected to the RFID table 114, a conductor ribbon 112 for the LCD display 48 (FIG. 7), and the main circuit board assembly 92. The second and third test tube racks 50 and 64 are shown positioned within the fraction collector 36. The fraction collector 36 is a 96 opening rack or any other appropriate size rack having the tube 84 within it and the test tube rack 50 is a 48 opening rack showing as an example a test tube 64 within it.

In operation, the RFID devices such as 40K (FIG. 7) contain an identification of the test tube rack by the arrangement of tubes in the sizes within it so that when they register with the appropriate RFID reader 56A (FIG. 7), 56B and 56C the reader can indicate to the main circuit board 92 that the test tube rack is in place so as to control the distributor arm 60 to distribute effluent in the proper tubes or to waste. The RFID reader 56A, 56B or 56C may also contain information about the size of the test tubes 50 and 84 in the test tube racks so that the controller 18 (FIG. 1) may receive this information from the RFID reader 56A and initiate a program that will move the distributor arm 60 to collect the sample if necessary in successive tubes and avoid overflow. The RFID devices such as the RFID wireless communication device 40K in the second test tube rack 52 (FIG. 7) can identify the samples collected in the test tubes, provide the test tube configuration and identify the fractions or the like as well as including user identification so that the test tube rack may continue to supply user information to other processing units as needed and control the distribution of the samples. Moreover, this information may be utilized by transfer devices to transfer the samples for use with other analytical equipment such as spectrometers or the like and may be used with corresponding devices in the spectrometer for further processing and transfer of information such as to electronic notebooks.

The wireless communications system in the preferred embodiment uses RFID TAGS such as THE Q5 programmable RFID tags sold by Sokymat and operating at 125 KHz. The RFID reader modules are ID-Innovations ID-12. They are encoded to identify the two configurations, number of tubes and volume of the tubes.

Figure 9:
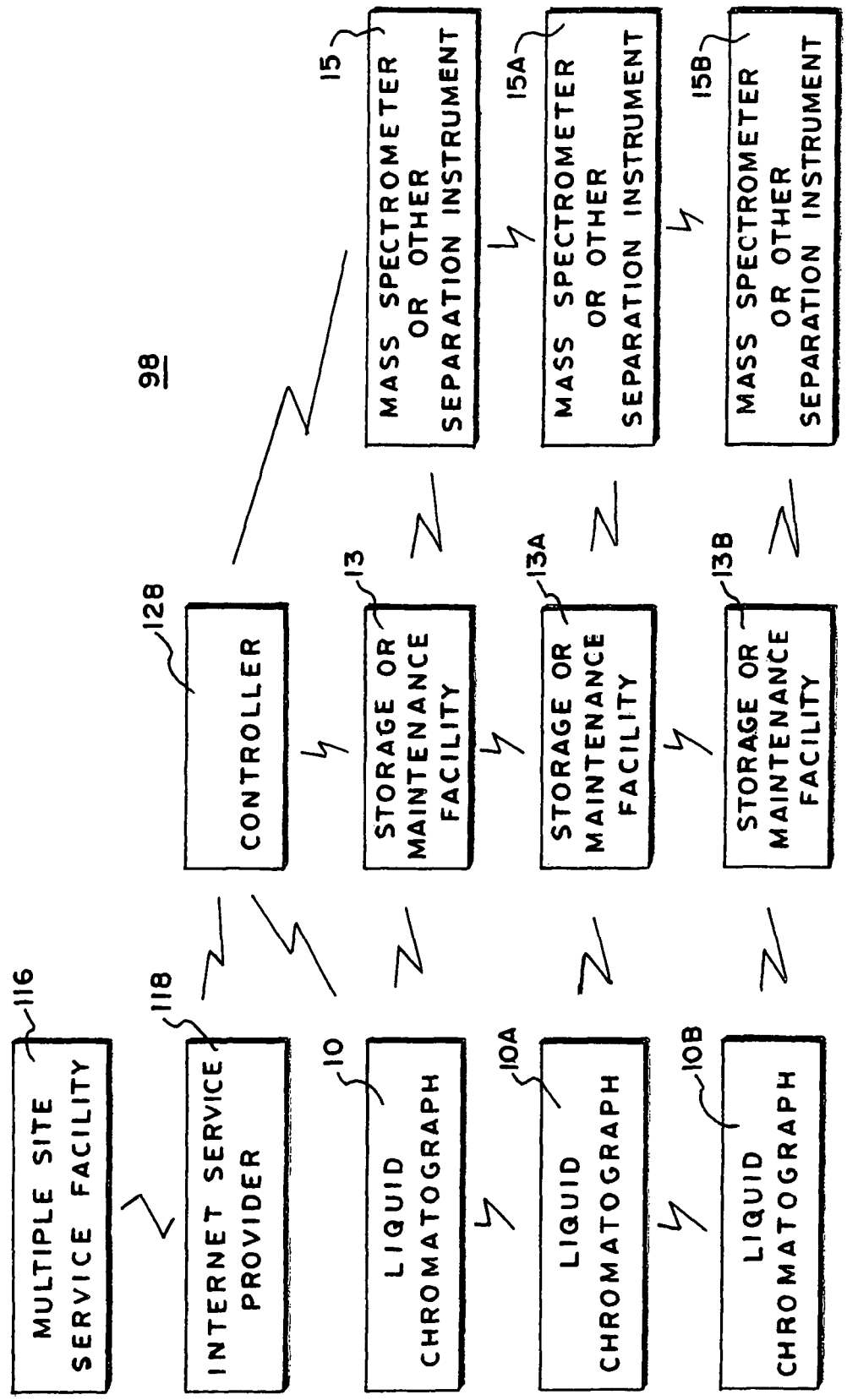
FIG. 9 is a block diagram of a system for remotely controlling and monitoring a plurality of liquid chromatographic systems or other multiple fraction arrangements or processes in accordance with an embodiment of the invention.

In FIG. 9, there is shown a block diagram of a system 98 for remotely controlling and monitoring a plurality of liquid chromatographic systems or other multiple fraction instruments or processes having a central controller 128 which may be a personal computer or other computer, a multiple site service facility 116 which may be the facility of a manufacturer that manufacturers the instrument and supplies parts and supplies for the instrument, an internet service provider 118, a plurality of the instruments such as the liquid chromatographs 10-10B, one or more storage or maintenance facility such as those shown at 13-13B and other instruments like the mass spectrometers or other separation instruments such as those shown at 15-15B for example. The component parts of the instruments 10-10B and 15-15B communicate with each other and may communicate with storage or maintenance facilities. For example, columns may be stored for use between runs using the column and these columns may be stored with information on them about the history of the column, including information about projects to which the column is dedicated or information about customers for whom the projects are being run or any other such relevant information. The same may be true of collection vessels or racks or the like. This information may also be transmitted to the central controller 128 and from there to an internet service provider 118 for transmission and gathering of data at a multiple site service facility 1 16.

The multiple site service facility 116 may maintain statistics on individual customers using a particular system so as to anticipate supplies the customer may need. Moreover, repair information may be transmitted such as for example if a chromatographic system 10-10B fails in some respect the wireless communication device on the instrument may detect the failure and the information transmitted by way of the central controller 128 to the multiple site service facility 116. For example, the multiple site service facility may have statistics indicating a particular customer is using a particular type of column at a fixed rate and has an inventory of a predetermined number of columns. With this information, the multiple site service facility 116 can predict when the customer will need more columns and contact the customer to arrange for sale of the columns. Similarly, the multiple site service facility 116 may determine statistically when certain components are likely to exceed their life. It may for example determine that a certain type of fraction collector is useful for a predetermined number of hours of operation from its statistical data base and when a particular fraction collector approaches that number, may notify the customer so as to be prepared for service or repurchase. The efficiency of the columns for certain chemistries and processes may be determined from statistics gathered from multiple stations. Customer specific information may be obtained and supplied to a customer or used in performing services for a customer such as default conditions, good manufacturing practices, billing information, IQ (installation qualifications), OQ (operation qualifications) and PQ (performance qualifications) including both test steps and results.

Figure 10:
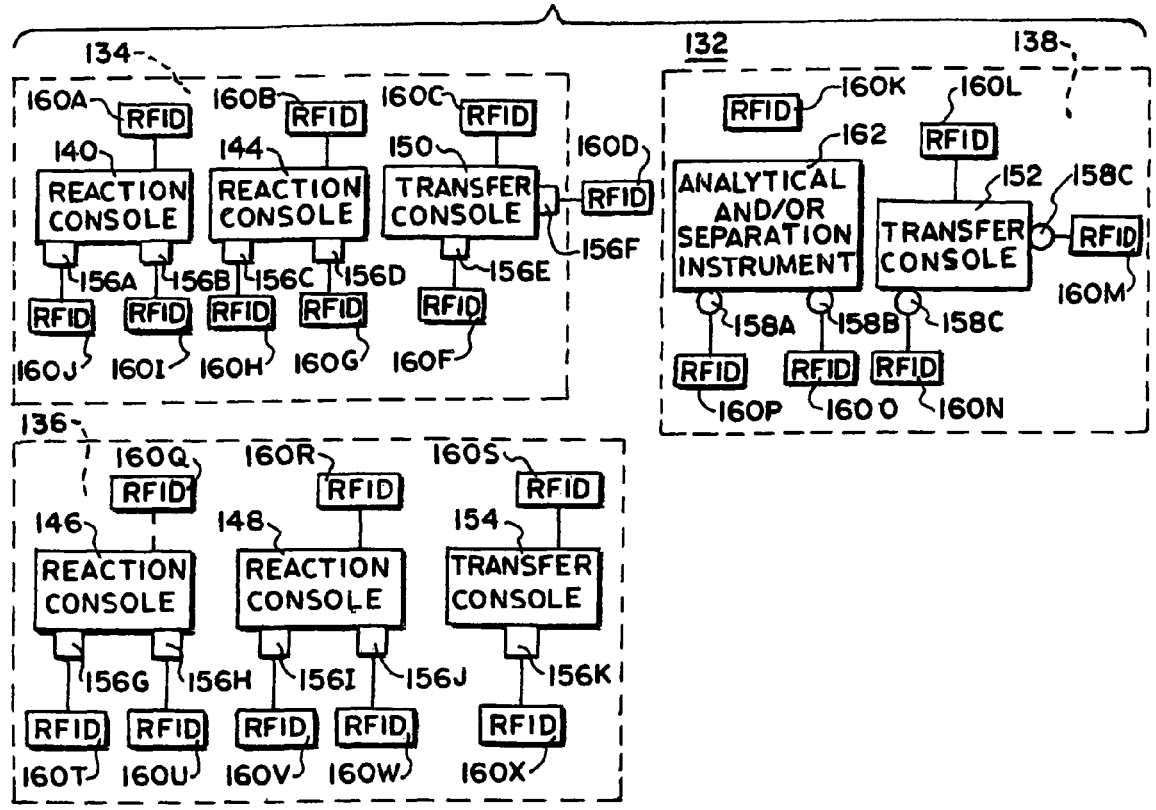
FIG. 10 is a block diagram of a chemical processing system in accordance with an embodiment of the invention.

In FIG. 10, there is shown a block diagram of a chemical processing system 132 having first and second chemical processing stations 134 and 136 and an analytical or separation station 138. The chemical processing stations 132 and 136 perform chemical operations including combinatorial chemical processes in which a range of known reagents or known quantities of reagents are sequentially applied to some material under temperature and time conditions to cause a reaction, or the time and temperatures are sequentially changed to arrive at the parameters for a preferred reaction. These stations include a mechanism for transferring the product of the reaction to another container or instrument for transferring to an analytical station for further analysis or purification or separation of the reaction product.

Within the chemical processing station 134, there are a plurality of reaction consoles such as 140 and 144 and similarly within the reaction station 136, there are a similar plurality of reaction consoles 146 and 148. Each of the reaction stations 134 and 136 also includes transfer consoles such as the transfer console 150 in reaction station 134 and the transfer console 154 in reaction station 136. The reaction stations apply reagents to chemical materials and maintain them for the proper time and at the proper temperature and pH for a desired reaction. They do this automatically and continuously and each include an appropriate wireless communication system such as 160A for the reaction consoles 140 and 144, wireless communication system 160Q for the reaction console 146 and wireless communication system 160R for the reaction console 148. These wireless communication systems transfer an identification of the substance being reacted upon and other information such as the reactants, time, temperature, the user or customer for whom the reaction is being performed and further reactions that are necessary in accordance with FDA standards to provide tamper-proof communication and reaction measures.

There are many different reaction consoles that may be used and are on sale but a suitable reaction console is disclosed in U.S. Pat. No. 4,168,955 issued to Robert W. Allington on Sep. 25, 1979, the disclosure of which is incorporated herein. Each of the chemical processing stations 134 and 136 also includes the transfer consoles 150 and 154 respectively and each of the transfer consoles 150 and 154 communicates with a corresponding one of the wireless communication systems 160C and 160S. These devices apply information relating to the reagent, the steps in using the reagent to prepare the reaction product and the reaction product and future operations such as the analysis or separation or purification required. This information is applied to transfer containers such as 156F and the information is applied to the transfer container 156F by a corresponding wireless communication system 160D.

These containers may be utilized by the analytical and or separation station 138 by being applied to an analytical or separation instrument 162 therein either manually or through robotics for analysis or for separation. This instrument 162 for example may be a liquid chromatograph capable of detecting and recognizing by the time of the peaks particular materials or capable of purification of separation of particular molecular species. The separation and analysis reaction may be transferred by a wireless communication system 160K communicating with the analytical or separation instrument 162. The purified substance and information concerning it may be transferred by the wireless communication system 160K to containers for the purified or separated material such as 160P and 160O in communication with their respective containers 158A and 158B. The containers 158A, 158B and 158C maybe transferred by a transfer console 152 to a transfer container 158D at the transfer console 152 and the wireless communication system 160L may transfer information to the wireless communication system 160M in communication with the container such as 158D shown in FIG. 10. With this arrangement, containers from the chemical processing station will have all of the necessary information on it for further use or further processing.

Figure 11:
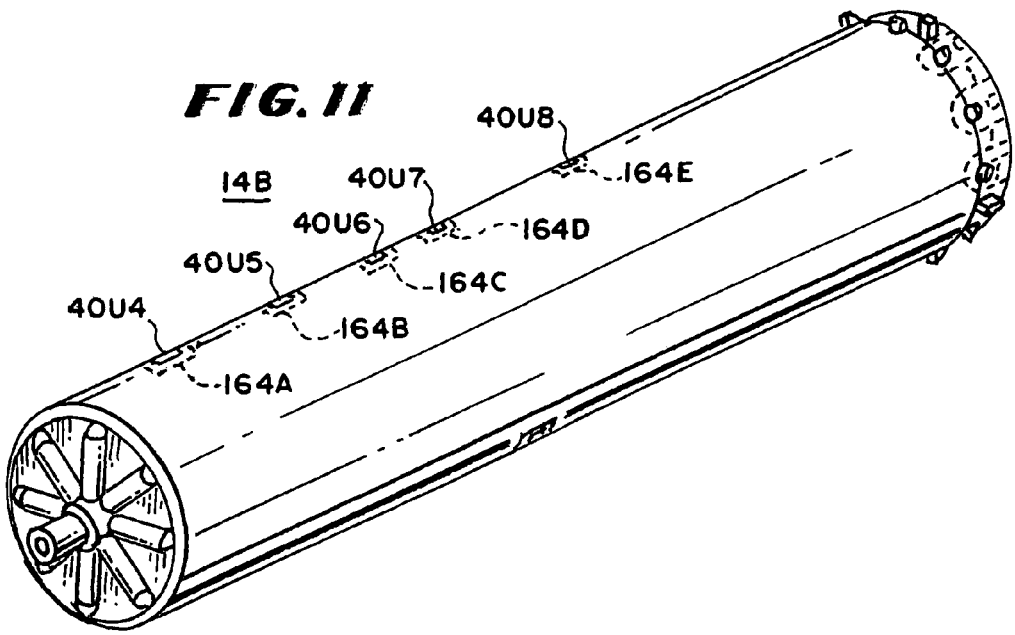
FIG. 11 is a chromatographic column having sensors for factors such as temperature, pressure, pH and the like in accordance with an embodiment of the invention.

In FIG. 11, there is shown a column 14B having a plurality of wireless communication devices 40U4-40U8, which in the preferred embodiment are RFID devices, spaced along its length and electrically connected for communication with sensors 164A-164E inside the column 14B. The sensors 164A-164E may sense characteristics within the column or may be spaced in the column to sense a characteristic of a wall of the column or the outside temperature as desired. In one embodiment, the sensors such as 164A-164E may be molded within the wall so that the sensors may be in contact with the contents of the column 14B but the column 14B remains sealed while the wireless communication devices 40U4-40U8 may transmit wirelessly outside the column 14B.

In some embodiments, instead of sensors and wireless communication devices spaced along the wall of the column, a transponder and wireless communication device may be located within the column. For example, a temperature transponder and wireless communication device may be encased in a protective casing and located within the packing of the column to sense temperature and transmit the temperatures outside of the column to provide feedback for controlling the temperature in the column. An external heater or cooling apparatus may be controlled by a temperature recorded in a wireless communication device and the transmitted temperature to heat or cool the column or the solvent being applied to the column to maintain the temperature within a desired range. One such communication device and suitable temperature sensor is manufactured by KSW Microtek within the KSW-VarioSens product line. These transponders are available from KSW Microtek; Manfred-Von-Ardenne-Ring 12 D-01099 Dresden,Germany.

In FIG. 12, there is shown a block diagram of a waste water sampler system 166 having a control system 168, one or more fill station drive motors 170, a pump station 174, a pump drive section 176, a driver 172 for the pump drive station 176 and a distributor 178. The pump station 174 is adapted to communicate with a water source 180 to sample water therefrom. To control the waste water sampler system 166, the control system 168 includes the CPU 182 connected for communication with a wireless communication device 188A, the display 184 connected for communication with the wireless communication device 188B and the keyboard 186 electrically connected to a wireless communication device 188C for communication therewith.

The control system 168 can be programmed to cause the pump station 174 to pump samples of water from the water source 180 by transmitting signals from the wireless communication device 188A to wireless communication device 188G that is connected for communication to the pump drive station 176. In response to signals transmitted by wireless communication device 188A from the control system 168, the pump station 174 pumps the samples into containers within the distributor 178. To control the fill station drive motor 170, the control system signals from the wireless communication device 188A to the wireless communication device 188E that is connected to communicate with the distributor 178 and by transmitting signals to the wireless control device 188D that is connected for communication to the fill station drive motor 170. The bottles are usually standard sized and shaped sample bottles within the distributor 178 but include within them wireless communication devices.

These wireless communication devices include a nonvolatile memory that receives signals from the CPU 182 and records the time and amount of water deposited into the containers for future reference. The nonvolatile memory also records the temperature of the water and a log of sample temperature from the time of sampling until analysis. The temperature measurement can also be used to provide feedback for non-contact closed loop control of sample temperature by controlling a heating or cooling device. If the container is in a container or rack, the weight of the container will be an indication of the amount of sample and may be weighed by a simple scale at the bottom of the container. The scale may be connected to a wireless communication device and provide a convenient readout of the amount of sample on a monitor to control in a feedback manner the drawing of the sample.

The control system 168 controls the operation to automatically fill a series of containers so that the distributor 178 includes sample containers that may be identified as to the location where the water was drawn, the time the water was drawn, the customer for which the water was drawn, the source of the water, and the test steps to be performed on the water. The control system 168 includes a central processor unit 182 with a typical display and/or printing unit shown at 184 and typical input units such as a keypad or electrical communication jack shown at 186. The control system 168 is programmed and contains the necessary interfaces to coordinate the operation of the pump station 174, the distributor 178 and the fill station drive motor 170 in such a way as to provide flexibility in drawing samples. It coordinates the operation of the individual components to properly fill containers while maintaining the integrity of volatile substances within the liquids for later testing.

In FIG. 13, there is shown a block diagram of a sampling arrangement including a central station 190 and a plurality of remote sites with samplers illustrated at 192. The central station 190 includes an ice source 196, the bottle carrier source 198, a container source 200, composite containers 204 and a plurality of shipping cartons from a shipping carton source 202. The samplers, periodic replacement ice, container carriers, containers and shipping cartons for the samples are moved from the central station 190 to each of the remote sites with samplers 192 for use and samples are removed from the remote sites and they are taken to the laboratory which may be at the central station such as shown at 206. At the testing laboratory 206, an RFID wireless communication device 208D is programmed with a test and the results and that program are transferred to the individual containers. The individual containers have on them, in addition to the source of the testing laboratory 206 which is introduced by the RFID wireless communication device 208E which is connected for communication with the console at the testing laboratory 206. The shipping carton source 202 is connected for communication with the wireless communication device 208C to maintain an inventory as cartons are removed and new empty cartons supplied. Similarly, the container source 200 is connected for communication to the RFID wireless communication device 208B which maintains an inventory of available containers by receiving information programmed on it as new containers are brought in and as old containers leave. The bottle carrier source 198 similarly keeps an inventory.

With this arrangement, different configurations of containers may be utilized with the same base at a plurality of different sites and the samples may be conveniently brought from the site to the appropriate location for the samples to be analyzed or utilized. In operation, a sampler is brought to the site and samples are drawn. A shipping carton container, carrier containers and ice are brought to the site. The container carrier is removed from the shipping carton, the ice is removed and the containers of sample are removed from the sampler. The container carrier, ice and containers are taken from the shipping carton and put into the sampler. The old container carrier, carriers and ice are put into the shipping carton and taken to the laboratory for analysis.

Each of the multiple fraction systems used above employ wireless communication devices such as radio frequency identification devices (RFID) to communicate between components, stations and consoles so as to provide instructions for operations, transfer information so as to maintain a record of operations that have been performed and are to be performed and record data.

Although a preferred embodiment of the invention has been described in substantial detail, many modifications and variations of the invention are possible in light of the above description. Accordingly, it is to be understood that, within the scope of the appended claims, the invention may be practiced other than as specifically described.

What is claimed is:

1. A method of tamper-proof environmental sampling comprising the steps of:
receiving at least one liquid fraction from a body of liquid, the receiving configured to maintain integrity of a substance within the liquid fraction;
receiving at least one container, the at least one container configured to be placed within a corresponding one of a plurality of container mounting fixtures, each of the container mounting fixtures adapted to receive the at least one container,
receiving information, the information comprising a first variable defining the liquid fraction, the first variable further including at least one of 1) a draw location, 2) a draw time and date, 3) a customer identification, 4) a source, 5) a temperature, and 6) a test step to be performed, and a second variable defining a location of the at least one container placed within one of the plurality of container mounting fixtures;
receiving wireless commands from a controller, the controller configured to wirelessly communicate via a wireless communication device, the wireless commands configured for a tamper-proof communication and reaction measure;
moving a movable fixture with at least one flow path to a position in proximity with the at least one container, the movable fixture configured to wirelessly communicate with the controller, the moving in response to a first wireless command from the controller, the first wireless command based in part on the second variable;
distributing a portion of the liquid fraction into one of the at least one container, the distributing in response to a second wireless command from the controller, the second wireless command based in part on the first variable;

providing a wireless movement feedback signal and a distribution feedback signal to the controller from the moving and the distributing;

comparing the wireless movement feedback signal and the distribution feedback signal to the first wireless command and the second wireless command; and providing an alarm if the comparing indicates an improper movement.

2. A method of tamper-proof environmental sampling in accordance with claim 1 wherein the second variable is wirelessly transmitted by a wireless communication device in proximity with one of a plurality of container mounting fixtures.

3. A method of tamper-proof environmental sampling in accordance with claim 1 further including the steps of receiving and recording the first variable and the second variable on a memory device attached to the at least one container, the receiving via a wireless communication signal.

* * * * *